US012721936B2

(12) United States Patent
Squitieri

(10) Patent No.: US 12,721,936 B2
(45) Date of Patent: Sep. 1, 2026

(54) APPROACHES TO MITIGATING PRESSURE APPLIED TO IMMOBILIZED PATIENTS UNDERGOING TREATMENT BY UNDERLYING SURFACES AND ASSOCIATED SYSTEMS

(71) Applicant: TurnCare, Inc., Palo Alto, CA (US)

(72) Inventor: Rafael Paolo Squitieri, Wilton, CT (US)

(73) Assignee: TurnCare, Inc., Palo Alto, CA (US)

( * ) Notice: Subject to any disclaimer, the term of this patent is extended or adjusted under 35 U.S.C. 154(b) by 3 days.

(21) Appl. No.: 18/967,423

(22) Filed: Dec. 3, 2024

(65) Prior Publication Data

US 2025/0090737 A1 Mar. 20, 2025

Related U.S. Application Data

(62) Division of application No. 17/067,216, filed on Oct. 9, 2020, now Pat. No. 12,178,949.

(51) Int. Cl.
*A61M 1/36* (2006.01)
*A61G 7/057* (2006.01)
(Continued)

(52) U.S. Cl.
CPC .......... *A61M 1/36* (2013.01); *A61G 7/05769* (2013.01); *A61G 13/1265* (2013.01);
(Continued)

(58) Field of Classification Search
CPC .... A61M 1/36; A61M 1/1698; A61M 1/3659; A61M 16/00; A61M 16/04;
(Continued)

(56) References Cited

U.S. PATENT DOCUMENTS 4,536,893 A 8/1985 Parravicini
4,567,887 A 2/1986 Couch
(Continued)

FOREIGN PATENT DOCUMENTS

DE 102012104243 A1 11/2012
DE 212014000239 U1 * 9/2016 ............ B60K 15/04
(Continued)

*Primary Examiner* — Justin C Mikowski
*Assistant Examiner* — Deborah Talitha Gedeon
(74) *Attorney, Agent, or Firm* — Perkins Coie LLP; Andrew T. Pettit

(57) ABSTRACT

Introduced here are pressure-mitigation apparatuses able to mitigate the pressure applied to a human body by the surface of an object. A controller device can be fluidically coupled to a pressure-mitigation device that includes a series of selectively inflatable chambers. When a pressure-mitigation device is placed between a human body and a surface, the controller device can continuously, intelligently, and autonomously circulate air through the chambers of the pressure-mitigation device. As further discussed below, the controller device may cause the chambers to be selectively inflated, deflated, or any combination thereof. Such an approach is useful in a variety of contexts. For example, pressure-mitigation apparatuses may be used to improve treatment of patients suffering from respiratory illnesses and patients who are partially or completely immobilized for extended durations (e.g., as part of a medical procedure).

16 Claims, 21 Drawing Sheets

(51) Int. Cl.

| | |
|---|---|
| ***A61G 13/12*** | (2006.01) |
| ***A61M 1/16*** | (2006.01) |
| ***A61M 16/00*** | (2006.01) |
| ***A61M 16/04*** | (2006.01) |
| ***A61M 60/38*** | (2021.01) |

(52) U.S. Cl.

CPC ........ *A61M 1/1698* (2013.01); *A61M 1/3659* (2014.02); *A61G 7/05776* (2013.01); *A61G 2200/325* (2013.01); *A61G 2200/327* (2013.01); *A61G 2203/12* (2013.01); *A61G 2210/00* (2013.01); *A61M 16/00* (2013.01); *A61M 16/04* (2013.01); *A61M 60/38* (2021.01)

(58) Field of Classification Search

CPC ............ A61G 7/05769; A61G 13/1265; A61G 7/05776; A61G 2200/325; A61G 2200/327; A61G 2203/12; A61G 2210/00

USPC ........... 5/713, 633, 634; 604/43; 128/204.18

See application file for complete search history.

(56) References Cited

U.S. PATENT DOCUMENTS

| | | | | |
|---|---|---|---|---|
| 4,799,276 | A | 1/1989 | Kadish | |
| 4,873,731 | A | 10/1989 | Williamson | |
| 5,092,007 | A | 3/1992 | Hasty | |
| 5,815,864 | A | 10/1998 | Sloop | |
| 6,273,810 | B1 | 8/2001 | Rhodes et al. | |
| 6,317,912 | B1 | 11/2001 | Graebe et al. | |
| 6,415,814 | B1 | 7/2002 | Hand et al. | |
| 6,855,158 | B2 | 2/2005 | Stolpmann | |
| 7,010,369 | B2 | 3/2006 | Borders et al. | |
| 7,017,195 | B2 | 3/2006 | Buckman et al. | |
| 7,219,380 | B2 | 5/2007 | Beck et al. | |
| 7,883,478 | B2 | 2/2011 | Skinner et al. | |
| 8,726,908 | B2 | 5/2014 | Squitieri | |
| 8,757,165 | B2 | 6/2014 | Squitieri | |
| 9,826,956 | B2 * | 11/2017 | Freeman ................ | A61B 7/008 |
| 9,901,491 | B2 | 2/2018 | Squitieri | |
| 9,931,238 | B2 | 4/2018 | Squitieri | |
| 10,064,784 | B2 | 9/2018 | Rawls-Meehan | |
| 2001/0016960 | A1 | 8/2001 | Grabell et al. | |
| 2002/0133877 | A1 | 9/2002 | Kuiper et al. | |
| 2002/0170117 | A1 | 11/2002 | Flick et al. | |
| 2004/0116898 | A1 | 6/2004 | Hawk | |
| 2004/0193084 | A1 | 9/2004 | Ravikumar | |
| 2004/0222611 | A1 | 11/2004 | Fenwick et al. | |
| 2005/0022305 | A1 | 2/2005 | Bieganek et al. | |
| 2005/0261656 | A1 | 11/2005 | Garcia et al. | |
| 2006/0064800 | A1 | 3/2006 | Freund | |
| 2007/0101505 | A1 | 5/2007 | Oprandi | |
| 2008/0098527 | A1 * | 5/2008 | Weedling ................. | A61G 7/07 5/633 |
| 2008/0142022 | A1 * | 6/2008 | Biondo ................ | A61G 7/1015 128/845 |
| 2008/0172797 | A1 | 7/2008 | Niels | |
| 2009/0144909 | A1 | 6/2009 | Skinner et al. | |
| 2009/0194115 | A1 | 8/2009 | Squitieri | |
| 2009/0217460 | A1 | 9/2009 | Bobey et al. | |
| 2011/0125330 | A1 | 5/2011 | Huber et al. | |
| 2011/0181394 | A1 | 7/2011 | Blair | |
| 2011/0296621 | A1 | 12/2011 | Mckenna | |
| 2012/0030878 | A1 | 2/2012 | Davenport et al. | |
| 2012/0090095 | A1 | 4/2012 | Fraser | |
| 2013/0019873 | A1 | 1/2013 | Choi et al. | |
| 2013/0255699 | A1 | 10/2013 | Squitieri | |
| 2014/0048081 | A1 | 2/2014 | Squitieri | |
| 2014/0050680 | A1 | 2/2014 | Garrett | |
| 2014/0059781 | A1 * | 3/2014 | Lafleche ............. | A61B 5/6892 5/713 |
| 2014/0290670 | A1 | 10/2014 | Squitieri et al. | |
| 2015/0034082 | A1 * | 2/2015 | Kimm .............. | A61M 16/0051 128/202.16 |
| 2015/0164677 | A1 | 6/2015 | Squitieri | |
| 2017/0246059 | A1 | 8/2017 | Chinn | |
| 2018/0301062 | A1 | 10/2018 | Curtis | |

FOREIGN PATENT DOCUMENTS

| | | | |
|---|---|---|---|
| EP | 1017348 | B1 | 11/2004 |
| EP | 2000057 | A1 | 12/2008 |
| WO | 9808473 | A1 | 3/1998 |
| WO | 2004105805 | A2 | 12/2004 |
| WO | 2005112855 | A2 | 12/2005 |
| WO | 2006131733 | A2 | 12/2006 |

* cited by examiner

Figure 10:
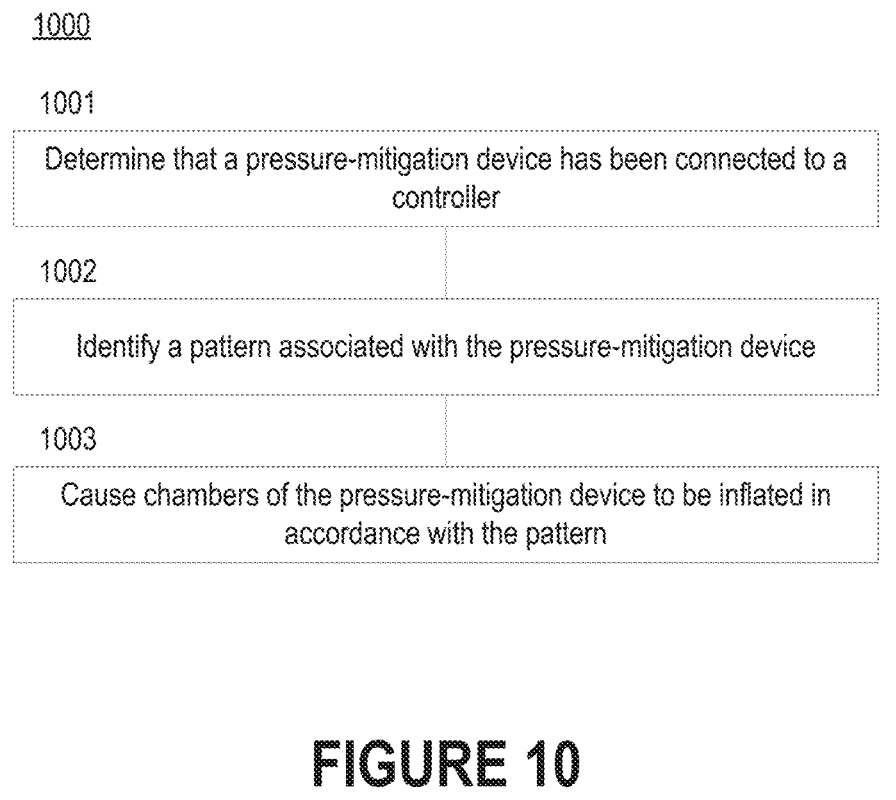

1000

1001

Determine that a pressure-mitigation device has been connected to a controller

1002

Identify a pattern associated with the pressure-mitigation device

1003

Cause chambers of the pressure-mitigation device to be inflated in accordance with the pattern

Figure 11:
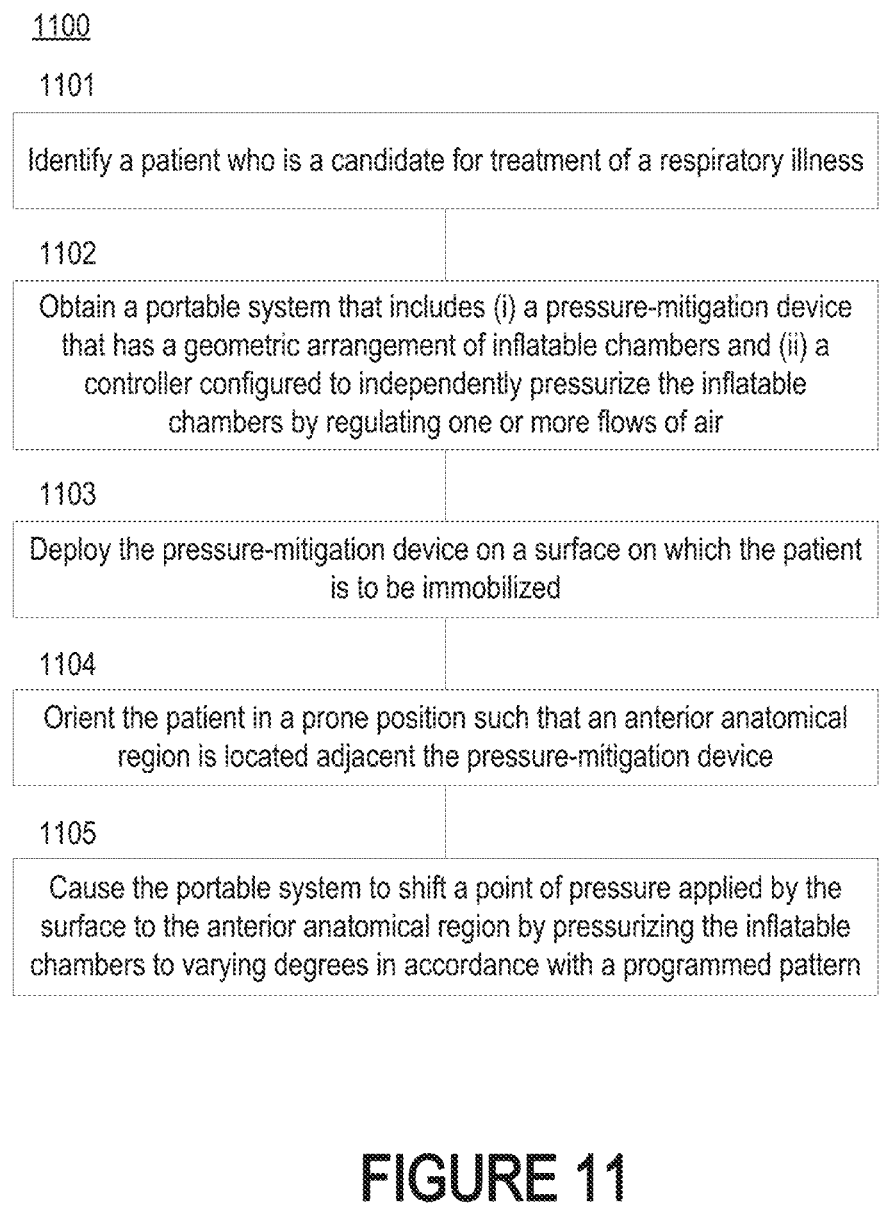

Identify a patient who is a candidate for treatment of a respiratory illness

1102

Obtain a portable system that includes (i) a pressure-mitigation device that has a geometric arrangement of inflatable chambers and (ii) a controller configured to independently pressurize the inflatable chambers by regulating one or more flows of air

1103

Deploy the pressure-mitigation device on a surface on which the patient is to be immobilized

1104

Orient the patient in a prone position such that an anterior anatomical region is located adjacent the pressure-mitigation device

1105

Cause the portable system to shift a point of pressure applied by the surface to the anterior anatomical region by pressurizing the inflatable chambers to varying degrees in accordance with a programmed pattern

Figure 12:
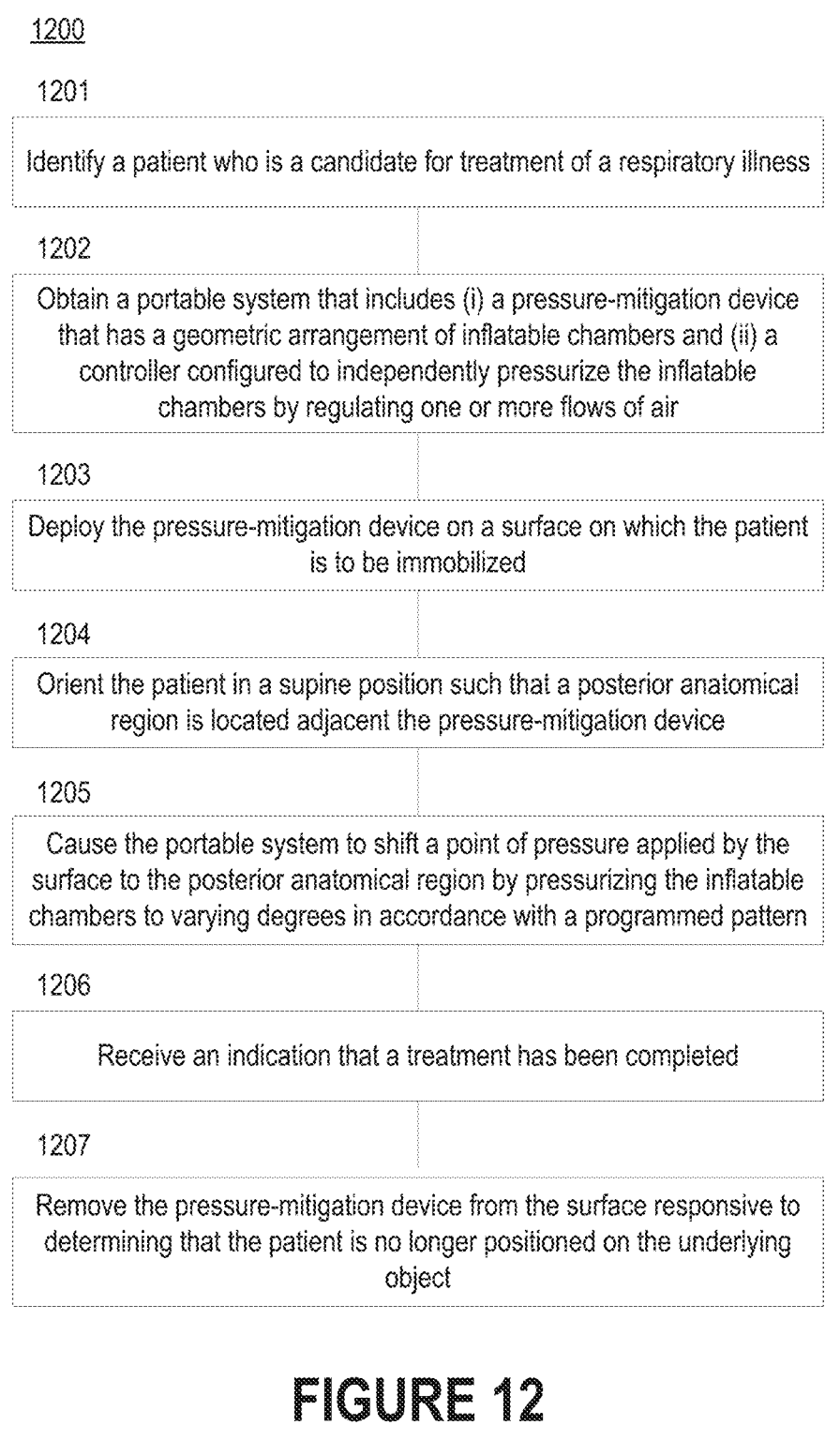

Identify a patient who is a candidate for treatment of a respiratory illness

1202

Obtain a portable system that includes (i) a pressure-mitigation device that has a geometric arrangement of inflatable chambers and (ii) a controller configured to independently pressurize the inflatable chambers by regulating one or more flows of air

1203

Deploy the pressure-mitigation device on a surface on which the patient is to be immobilized

1204

Orient the patient in a supine position such that a posterior anatomical region is located adjacent the pressure-mitigation device

1205

Cause the portable system to shift a point of pressure applied by the surface to the posterior anatomical region by pressurizing the inflatable chambers to varying degrees in accordance with a programmed pattern

1206

Receive an indication that a treatment has been completed

1207

Remove the pressure-mitigation device from the surface responsive to determining that the patient is no longer positioned on the underlying object

Figure 13:
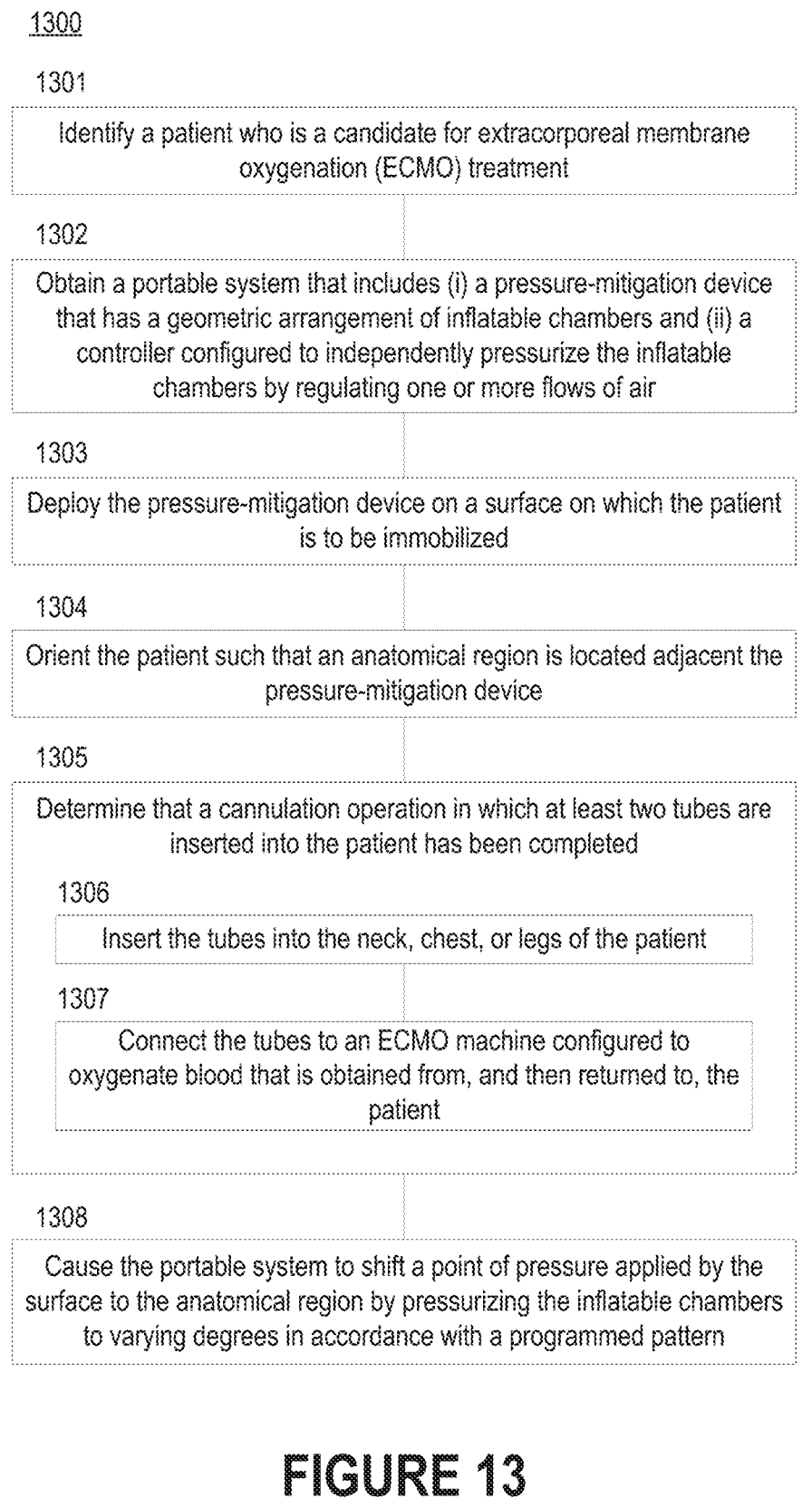

1301
Identify a patient who is a candidate for extracorporeal membrane oxygenation (ECMO) treatment 1302
Obtain a portable system that includes (i) a pressure-mitigation device that has a geometric arrangement of inflatable chambers and (ii) a controller configured to independently pressurize the inflatable chambers by regulating one or more flows of air 1303
Deploy the pressure-mitigation device on a surface on which the patient is to be immobilized 1304
Orient the patient such that an anatomical region is located adjacent the pressure-mitigation device 1305
Determine that a cannulation operation in which at least two tubes are inserted into the patient has been completed 1306
Insert the tubes into the neck, chest, or legs of the patient 1307
Connect the tubes to an ECMO machine configured to oxygenate blood that is obtained from, and then returned to, the patient 1308
Cause the portable system to shift a point of pressure applied by the surface to the anatomical region by pressurizing the inflatable chambers to varying degrees in accordance with a programmed pattern

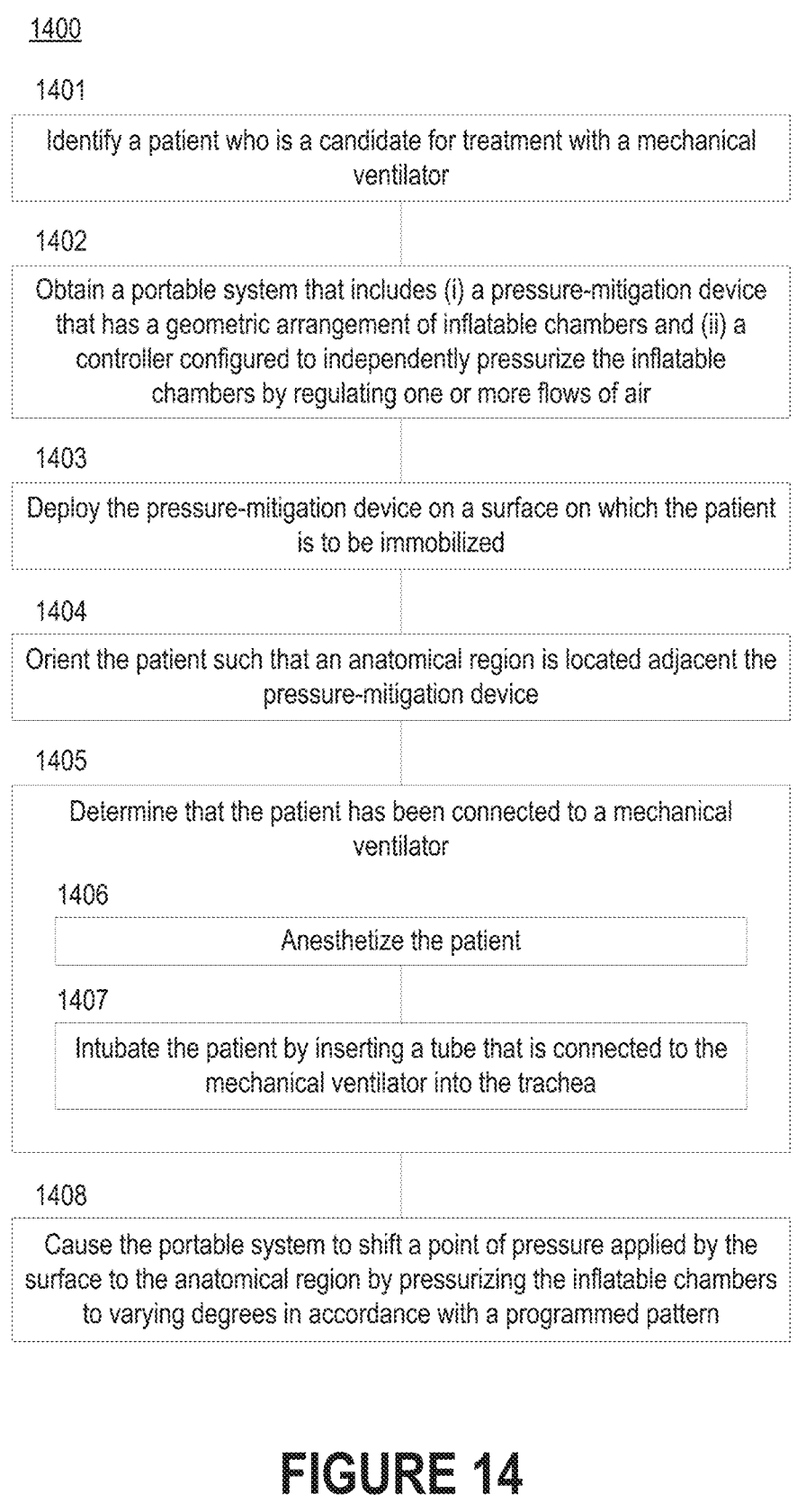

Identify a patient who is a candidate for treatment with a mechanical ventilator

1402

Obtain a portable system that includes (i) a pressure-mitigation device that has a geometric arrangement of inflatable chambers and (ii) a controller configured to independently pressurize the inflatable chambers by regulating one or more flows of air

1403

Deploy the pressure-mitigation device on a surface on which the patient is to be immobilized

1404

Orient the patient such that an anatomical region is located adjacent the pressure-mitigation device

1405

Determine that the patient has been connected to a mechanical ventilator

1406

Anesthetize the patient

1407

Intubate the patient by inserting a tube that is connected to the mechanical ventilator into the trachea

1408

Cause the portable system to shift a point of pressure applied by the surface to the anatomical region by pressurizing the inflatable chambers to varying degrees in accordance with a programmed pattern

FIGURE 14

APPROACHES TO MITIGATING PRESSURE APPLIED TO IMMOBILIZED PATIENTS UNDERGOING TREATMENT BY UNDERLYING SURFACES AND ASSOCIATED SYSTEMS

CROSS-REFERENCE TO RELATED APPLICATIONS

This application is a divisional of U.S. application Ser. No. 17/067,216, titled "PRESSURE-MITIGATION APPARATUSES FOR IMPROVED TREATMENT OF IMMOBILIZED PATIENTS AND ASSOCIATED SYSTEMS AND METHODS" and filed Oct. 9, 2020, which is incorporated by reference herein in its entirety.

TECHNICAL FIELD

Various embodiments concern pressure-mitigation apparatuses able to mitigate the pressure applied to a human body by the surface of an object.

BACKGROUND

Pressure injuries—sometimes referred to as "decubitus ulcers," "pressure ulcers," "pressure sores," or "bedsores"—may occur as a result of steady pressure being applied in one location along the surface of the human body for a prolonged period of time. Regions with bony prominences are especially susceptible to pressure injuries. Pressure injuries are most common in individuals who are completely immobilized (e.g., on an operating table, bed, or chair) or have impaired mobility. These individuals may be older, malnourished, or incontinent, all factors that predispose the human body to formation of pressure injuries.

These individuals are often not ambulatory, so they sit or lie for prolonged periods of time in the same position. Moreover, these individuals may be unable to reposition themselves to alleviate pressure. Consequently, pressure on the skin and underlying soft tissue may eventually result in inadequate blood flow to the area, a condition referred to as "ischemia," thereby resulting in damage to the skin or underlying soft tissue. Pressure injuries can take the form of a superficial injury to the skin or a deeper ulcer that exposes the underlying tissues and places the individual at risk for infection. The resulting infection may worsen, leading to sepsis or even death in some cases.

There are various technologies on the market that profess to prevent pressure injuries. However, these conventional technologies have many deficiencies. For instance, these conventional technologies are unable to control the spatial relationship between a human body and a support surface (or simply "surface") that applies pressure to the human body. Consequently, individuals that use these conventional technologies may still develop pressure injuries or suffer from related complications.

BRIEF DESCRIPTION OF THE DRAWINGS

FIG. 10 is a flow diagram of a process for varying the pressure in the chambers of a pressure-mitigation device that is positioned between a human body and a surface in accordance with embodiments of the present technology.

FIG. 11 is a flow diagram of a process for improved treatment of a patient suffering from a respiratory illness.

FIG. 12 is a flow diagram of another process for improved treatment of a patient suffering from a respiratory illness.

FIG. 13 is a flow diagram of a process for improved treatment of a patient undergoing extracorporeal membrane oxygenation (ECMO) treatment.

FIG. 14 is a flow diagram of a process for improved treatment of a patient presently being treated with a mechanical ventilator.

Figure 1A:
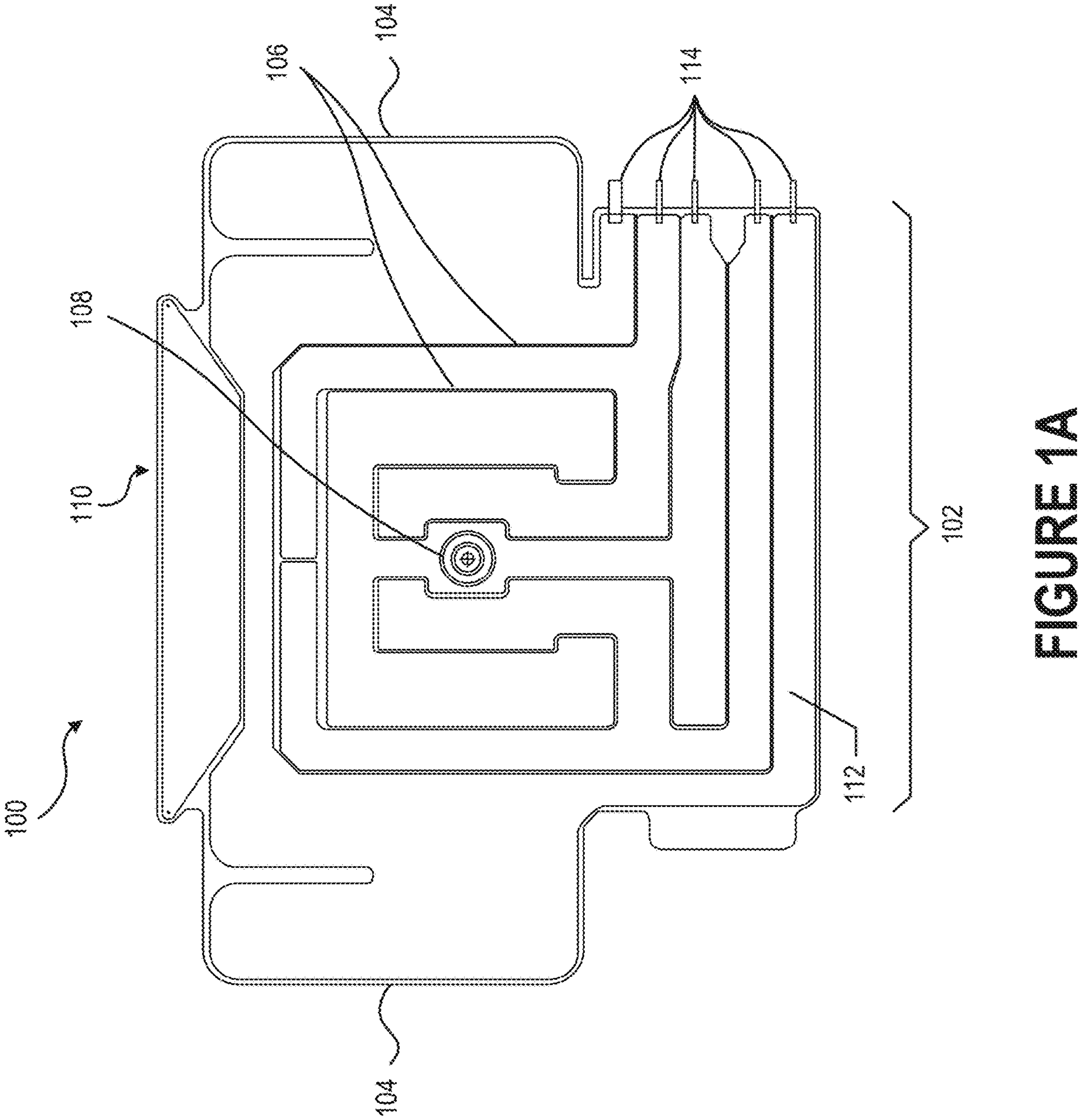
FIGS. 1A-B are top and bottom views, respectively, of a pressure-mitigation device able to relieve the pressure on an anatomical region applied by the surface of an elongated object in accordance with embodiments of the present technology.

Various features of the technologies described herein will become more apparent to those skilled in the art from a study of the Detailed Description in conjunction with the drawings. Embodiments are illustrated by way of example and not limitation in the drawings. While the drawings depict various embodiments for the purpose of illustration, those skilled in the art will recognize that alternative embodiments may be employed without departing from the principles of the technologies. Accordingly, while specific embodiments are shown in the drawings, the technology is amenable to various modifications.

DETAILED DESCRIPTION

The term "pressure injury" refers to a localized region of damage to the skin and/or underlying tissue that results from contact pressure (or simply "pressure") on the corresponding anatomical region of the human body. Pressure injuries will often form over bony prominences, such as the skin and soft tissue overlying the sacrum, coccyx, heels, or hips. However, other sites may also be affected. For instance, pressure injuries may form on the elbows, knees, ankles, shoulders, abdomen, back, or cranium. Pressure injuries may develop when pressure is applied to the blood vessels in soft tissue in such a manner that blood flow to the soft tissue is at least partially obstructed (e.g., due to the pressure exceeding the capillary filling pressure), and ischemia results at the site when such obstruction occurs for an extended duration. Accordingly, pressure injuries are normally observed on individuals who are mobility impaired, immobilized, or sedentary for prolonged periods of times.

Once pressure injuries have formed, the healing process is normally slow. For example, when pressure is relieved from the site of a pressure injury, the body will rush blood (with proinflammatory mediators) to that region to perfuse the area with blood. The sudden reperfusion of the damaged (and previously ischemic) region has been shown to cause an inflammatory response, brought on by the proinflammatory mediators, that can actually worsen the pressure injury and prolong recovery. Moreover, in some cases, the proinflammatory mediators may spread through the blood stream beyond the site of the pressure injury to cause a systematic inflammatory response (also referred to as a "secondary inflammatory response"). The secondary inflammatory response caused by the proinflammatory mediators has been shown to exacerbate existing conditions and/or trigger new conditions, thereby slowing recovery. Recovery can also be prolonged by factors that are frequently associated with individuals who are prone to pressure injuries, such as old age, immobility, preexisting medical conditions (e.g., arteriosclerosis, diabetes, or infection), smoking, and medications (e.g., anti-inflammatory drugs). Inhibiting the formation of pressure injuries (and reducing the prevalence of proinflammatory mediators) can enhance and expedite many treatment processes, especially for those individuals whose mobility is impaired during treatment.

Introduced here, therefore, are pressure-mitigation devices able to mitigate the pressure applied to a human body by the surface of an object (also referred to as a "structure"). A controller device (or simply "controller") can be fluidically coupled to a pressure-mitigation device (also referred to as a "pressure-mitigation apparatus" or a "pressure-mitigation pad") that includes a series of selectively inflatable chambers (also referred to as "cells" or "compartments"). When a pressure-mitigation device is placed between a human body and a surface, the controller can continuously, intelligently, and autonomously circulate air through the chambers of the pressure-mitigation device. As further discussed below, the controller may cause the chambers to be selectively inflated, deflated, or any combination thereof.

At a high level, the present disclosure concerns systems that comprise a pressure-mitigation device with inflatable chambers whose pressure can be regulated by a controller. These systems can be used to manage patients in an attempt to prevent and/or treat pressure injuries, as well as improve approaches to patient management by promoting early mobilization to aid in (and expedite) recovery. As further discussed below, the inflatable chambers can be designed and arranged so as to facilitate alignment of a given anatomical region (e.g., the sacral region) with the pressure-mitigation device. For example, the inflatable chambers may be intertwined around an epicenter in a geometric pattern based on the internal anatomy of the given anatomical region. When the inflatable chambers of the pressure-mitigation device are pressurized in accordance with the programmed (e.g., in terms of time and pressure) pattern executed by the controller, a patient-surface interaction is produced that emulates the interactions seen in healthy (e.g., mobile) individuals. However, instead of the patient periodically moving herself away from the surface to adjust contact pressure applied by the surface, the pressure-mitigation device shifts the patient. Accordingly, the pressure-mitigation device, in conjunction with the controller, can mimic the micro-adjustments that healthy individuals regularly complete. This creates a scenario in which a patient can remain partially or entirely motionless for an extended period of time, yet physiologically the net pressure effect on the patient is roughly the same as if the patient had maintained more natural motion (e.g., performed micro-adjustments). Such an approach prevents prolonged tissue compression, which can lead to ischemia and reperfusion injuries that result in lasting tissue damage (e.g., ulcers) and other adverse systemic health consequences.

By controllably varying the pressure in the series of chambers, the controller can move the main point of pressure applied by the surface to different regions across the human body. For example, the controller may cause the main point of pressure applied by the surface to be moved amongst a plurality of predetermined anatomic locations by sequentially varying the level of inflation of (and pressure in) predetermined subsets of chambers. Such an approach results in pressure gradients being created across the human body. In some embodiments, the controller controls the pressure of chambers located beneath specific anatomic locations for specific durations in order to move point(s) of pressure applied by the underlying surface around the anatomy in a precise manner such that specific portions of the anatomy (e.g., the tissue adjacent to bony prominences) do not experience direct pressure for an extended duration. The relocation of the pressure point(s) avoids vascular compression for sustained periods of time, inhibits ischemia, and reduces the incidence of pressure injuries.

Such an approach to mitigating pressure is useful in various contexts. As an example, assume that an individual has been identified as a candidate for treatment of a respiratory illness. The respiratory illness could be a chronic respiratory illness or an acute respiratory illness. In such a scenario, a medical professional may obtain a portable system comprised of a pressure-mitigation device and a controller. Examples of medical professionals include doctors, nurses, therapists, and the like. The medical professional can deploy the pressure-mitigation device on a surface on which the individual is to be immobilized, either partially or entirely, and then orient the individual on top of the pressure-mitigation device. Thereafter, the medical professional can cause the portable system to shift a point of pressure applied by the surface to the individual by pressurizing the inflatable chambers of the pressure-mitigation device to varying degrees in accordance with a programmed pattern. For example, the medical professional may initiate pressurization of the inflatable chambers by indicating that treatment should begin via the controller.

The programmed pattern may be associated with a particular anatomical region on which pressure is to be relieved. For example, if the pressure-mitigation device is to relieve pressure on a living body in the supine position, then the controller may pressurize the chambers in accordance with a programmed pattern associated with the sacral region. As another example, if the pressure-mitigation device is to relieve pressure on a living body in the prone position, then the controller may pressurize the chambers in accordance with a programmed pattern associated with the thoracic region. As another example, if the pressure-mitigation device is to relieve pressure on a living body in the sitting position, then the controller may pressurize the chambers in accordance with a programmed pattern associated with the gluteal region.

In some embodiments, the medical professional may orient the individual in the prone position such that an anterior anatomical region is located adjacent the pressure-mitigation device. In other embodiments, the medical professional may orient the individual in the supine position such that a posterior anatomical region is located adjacent the pressure-mitigation device. Whether the individual is oriented in the prone or supine position may depend on the therapy recommended for treatment of the respiratory illness.

Embodiments may be described with reference to particular anatomical regions, treatment regimens, computer programs, etc. However, those skilled in the art will recognize that the features are similarly applicable to other anatomical regions, treatment regimens, computer programs, etc. As an example, embodiments may be described in the context of a pressure-mitigation device that is positioned adjacent to an anterior anatomical region of an individual oriented in the prone position. However, aspects of those embodiments may apply to a pressure-mitigation device that is positioned adjacent to a posterior anatomical region of an individual oriented in the supine position.

While embodiments may be described in the context of machine-readable instructions, aspects of the technology can be implemented via hardware, firmware, or software. As an example, a controller may execute instructions for determining an appropriate pressure for an inflatable chamber based on inputs such as the weight of the individual, the level of immobility, the duration of immobility, etc.

Terminology

References in this description to "an embodiment" or "one embodiment" means that the feature, function, structure, or characteristic being described is included in at least one embodiment of the technology. Occurrences of such phrases do not necessarily refer to the same embodiment, nor are they necessarily referring to alternative embodiments that are mutually exclusive of one another.

Unless the context clearly requires otherwise, the terms "comprise," "comprising," and "comprised of" are to be construed in an inclusive sense rather than an exclusive or exhaustive sense (i.e., in the sense of "including but not limited to"). The term "based on" is also to be construed in an inclusive sense rather than an exclusive or exhaustive sense. Thus, unless otherwise noted, the term "based on" is intended to mean "based at least in part on."

The terms "connected," "coupled," or any variant thereof is intended to include any connection or coupling between two or more elements, either direct or indirect. The connection/coupling can be physical, logical, or a combination thereof. For example, objects may be electrically or communicatively coupled to one another despite not sharing a physical connection.

The term "module" refers broadly to software components, firmware components, and/or hardware components. Modules are typically functional components that generate output(s) based on specified input(s). A computer program may include one or more modules. Thus, a computer program may include multiple modules responsible for completing different tasks or a single module responsible for completing all tasks.

When used in reference to a list of multiple items, the term "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Overview of Pressure-Mitigation Devices

A pressure-mitigation device includes a plurality of chambers (also referred to as "cells" or "compartments") into which air can flow. Each chamber may be associated with a discrete flow of air so that the pressure in the plurality of chambers can be varied as necessary. When placed on the surface of an object on which a human body rests, the pressure-mitigation device can vary the pressure on an anatomical region by controllably inflating chamber(s) and/or deflating chamber(s) to create pressure gradients. Several examples of pressure-mitigation devices are described below with respect to FIGS. 1A-3. Unless otherwise noted, any features described with respect to one embodiment are equally applicable to other embodiments. Some features have only been described with respect to a single embodiment for the purpose of simplifying the present disclosure.

Figure 1B:
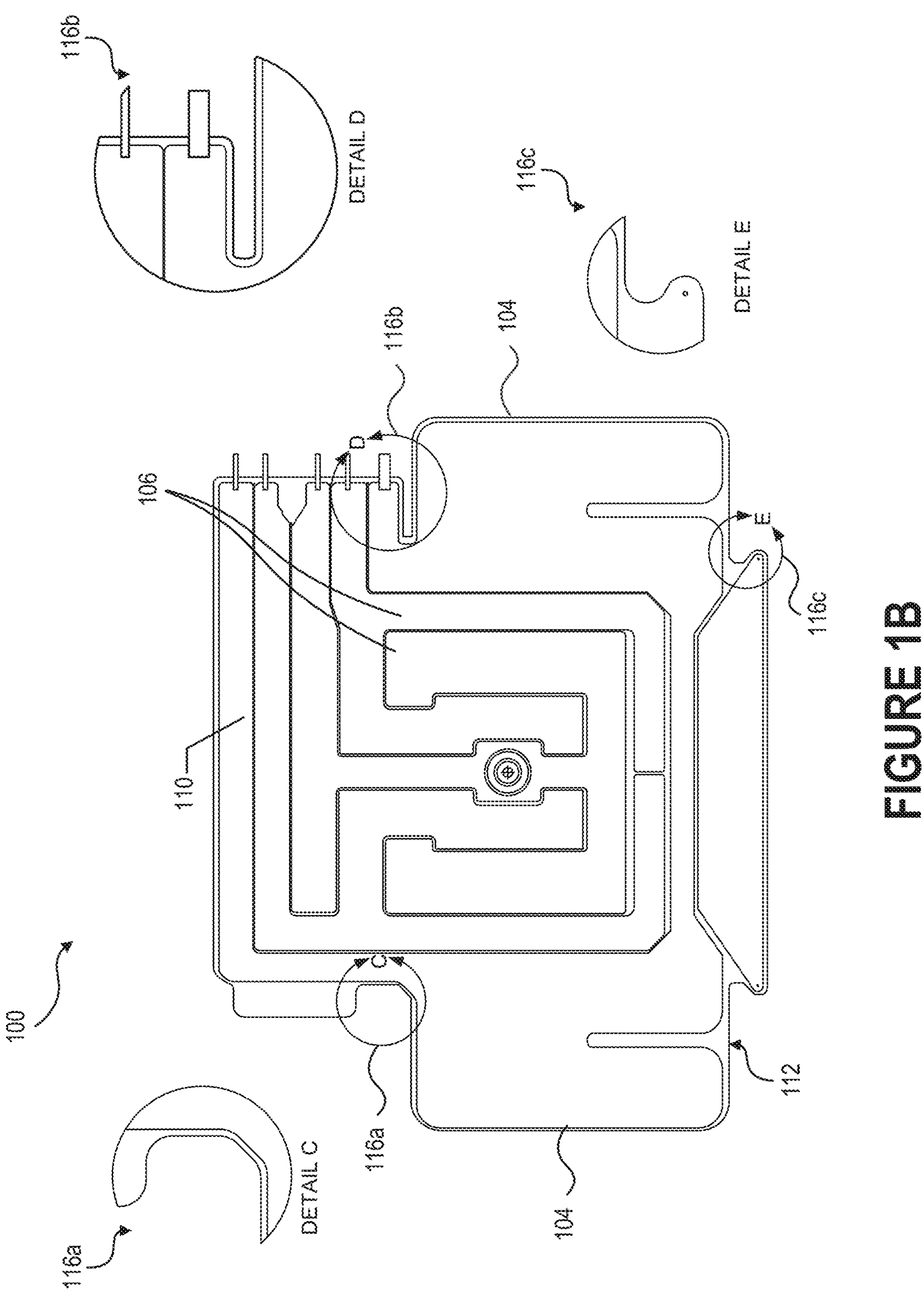

FIGS. 1A-B are top and bottom views, respectively, of a pressure-mitigation device 100 able to relieve the pressure on an anatomical region applied by the surface of an elongated object in accordance with embodiments of the present technology. While the pressure-mitigation device 100 may be described in the context of elongated objects, such as mattresses, stretchers, operating tables, and procedure tables, the pressure-mitigation device 100 could be deployed on non-elongated objects. In some embodiments, the pressure-mitigation device 100 is secured to a support surface using an attachment apparatus. In other embodiments, the pressure-mitigation device 100 is placed in direct contact with the surface without any attachment apparatus therebetween. For example, the pressure-mitigation device 100 may have a tacky substance deposited along at least a portion of its outer surface that allows it to temporarily adhere to the surface. Examples of tacky substances include latex, urethane, and silicone rubber.

As shown in FIG. 1A, the pressure-mitigation device 100 can include a central portion 102 (also referred to as a "contact portion") that is positioned alongside at least one side support 104. Here, a pair of side supports 104 are arranged on opposing sides of the central portion 102. However, some embodiments of the pressure-mitigation device 100 do not include any side supports. For example, the side support(s) 104 may be omitted when the individual is medically immobilized (e.g., under anesthesia, in a medically induced coma, etc.) and/or physically restrained by underlying object (e.g., by rails along the side of a bed, armrests along the side of a chair, etc.) or some other structure (e.g., physical restraints, casts, etc.).

The pressure-mitigation device 100 includes a series of chambers 106 whose pressure can be individually varied. In some embodiments, the series of chambers 106 are arranged in a geometric pattern designed to relieve pressure on specific anatomical region(s) of a human body. As noted above, when placed between the human body and a surface, the pressure-mitigation device 100 can vary the pressure on these specific anatomical region(s) by controllably inflating and/or deflating chamber(s).

In some embodiments, the series of chambers 106 are arranged such that pressure on a given anatomical region is mitigated when the given anatomical region is oriented over a target region 108 of the geometric pattern. As shown in FIGS. 1A-B, the target region 108 may be representative of a central point of the pressure-mitigation device 100 to appropriately position the anatomy of the human body with respect to the pressure-mitigation device 100. For example, the target region 108 may correspond to an epicenter of the geometric pattern. However, the target region 108 may not necessarily be the central point of the pressure-mitigation device 100, particularly if the series of chambers 106 are positioned in a non-symmetric arrangement. The target region 108 may be visibly marked so that an individual can readily align the target region 108 with a corresponding anatomical region of the human body to be positioned thereon. Thus, the pressure-mitigation device 100 may include a visual element representative of the target region 108 to facilitate alignment with the corresponding anatomical region of the human body. The individual could be a physician, nurse, caregiver, or the patient.

The pressure-mitigation device 100 can include a first portion 110 (also referred to as a "first layer" or "bottom layer") designed to face a surface and a second portion 112 (also referred to as a "second layer" or "top layer") designed to face the human body supported by the surface. In some embodiments, the pressure-mitigation device 100 is deployed such that the first portion 110 is directly adjacent to the surface. For example, the first portion 110 may have a tacky substance deposited along at least a portion of its exterior surface that facilitates temporarily adhesion to the support surface. In other embodiments, the pressure-mitigation device 100 is deployed such that the first portion 110 is directly adjacent to an attachment apparatus designed to help secure the pressure-mitigation device 100 to the support surface. The pressure-mitigation device 100 may be constructed of various materials, and the material(s) used in the construction of each component of the pressure-mitigation device 100 may be chosen based on the nature of the body contact, if any, to be experienced by the component. For example, because the second portion 112 will often be in direct contact with the skin, it may be comprised of a soft fabric or a breathable fabric (e.g., comprised of moisture-wicking materials or quick-drying materials, or having perforations). In some embodiments, an impervious lining (e.g., comprised of polyurethane) is secured to the inside of the second portion 112 to inhibit fluid (e.g., sweat) from entering the series of chambers 106. As another example, if the pressure-mitigation device 100 is designed for deployment beneath a cover (e.g., a bed sheet), then the second portion 112 may be comprised of a flexible, liquid-impervious material, such as polyurethane, polypropylene, silicone, or rubber. The first portion 110 may also be comprised of a flexible, liquid-impervious material.

The series of chambers 106 may be formed via interconnections between the first and second portions 110, 112. For example, the first and second portions 110, 112 may be bound directly to one another, or the first and second portions 110, 112 may be bound to one another via one or more intermediary layers. In the embodiment illustrated in FIGS. 1A-B, the pressure-mitigation device 100 includes an "M-shaped" chamber intertwined with two "C-shaped" chambers that face one another. Such an arrangement has been shown to effectively mitigate the pressure applied to the sacral region of a human body in the supine position by a support surface when the pressure in these chambers is alternated. The series of chambers 106 may be arranged differently if the pressure-mitigation device 100 is designed for an anatomical region other than the sacral region, or if the pressure-mitigation device 100 is to be used to support a human body in a non-supine position (e.g., a prone position or sitting position). Generally, the geometric pattern of chambers 106 is designed based on the internal anatomy (e.g., the muscles, bones, and vasculature) of the anatomical region on which pressure is to be relieved.

The person using the pressure-mitigation device 100 and/or the caregiver (e.g., a nurse, physician, family member, etc.) may be responsible for actively orienting the anatomical region of the human body lengthwise over the target region 108 of the geometric pattern. If the pressure-mitigation device 100 includes one or more side supports 104, the side support(s) 104 may actively orient or guide the anatomical region of the human body laterally over the target region 108 of the geometric pattern. In some embodiments the side support(s) 104 are inflatable, while in other embodiments the side support(s) 104 are permanent structures that protrude from one or both lateral sides of the pressure-mitigation device 100. For example, at least a portion of each side support may be stuffed with cotton, latex, polyurethane foam, or any combination thereof.

As further described below with respect to FIGS. 6A-C, a controller can separately control the pressure in each chamber (as well as the side supports 104, if included) by providing a discrete airflow via one or more corresponding valves 114. In some embodiments, the valves 114 are permanently secured to the pressure-mitigation apparatus 100 and designed to interface with tubing that can be readily detached (e.g., for easier transport, storage, etc.). Here, the pressure-mitigation device 100 includes five valves 114. Three valves are fluidically coupled to the series of chambers 106, and two valves are fluidically coupled to the side supports 104. Other embodiments of the pressure-mitigation apparatus 100 may include more than five valves or less than five valves. For example, the pressure-mitigation device 100 may be designed such that a pair of side supports 104 are pressurized via a single airflow received via a single valve.

In some embodiments, the pressure-mitigation device 100 includes one or more design features 116*a-c* designed to facilitate securement of the pressure-mitigation device 100 to the surface of an object and/or an attachment apparatus. As illustrated in FIG. 1B, for example, the pressure-mitigation device 100 may include three design features 116*a-c*, each of which can be aligned with a corresponding structural feature that is accessible along the surface of the object or the attachment apparatus. For example, each design feature 116*a-c* may be designed to at least partially envelope a structural feature that protrudes upward. One example of such a structural feature is a rail that extends along the side of a bed. The design feature(s) 116*a-c* may also facilitate proper alignment of the pressure-mitigation device 100 with the surface of the object or the attachment apparatus.

Figure 2A:
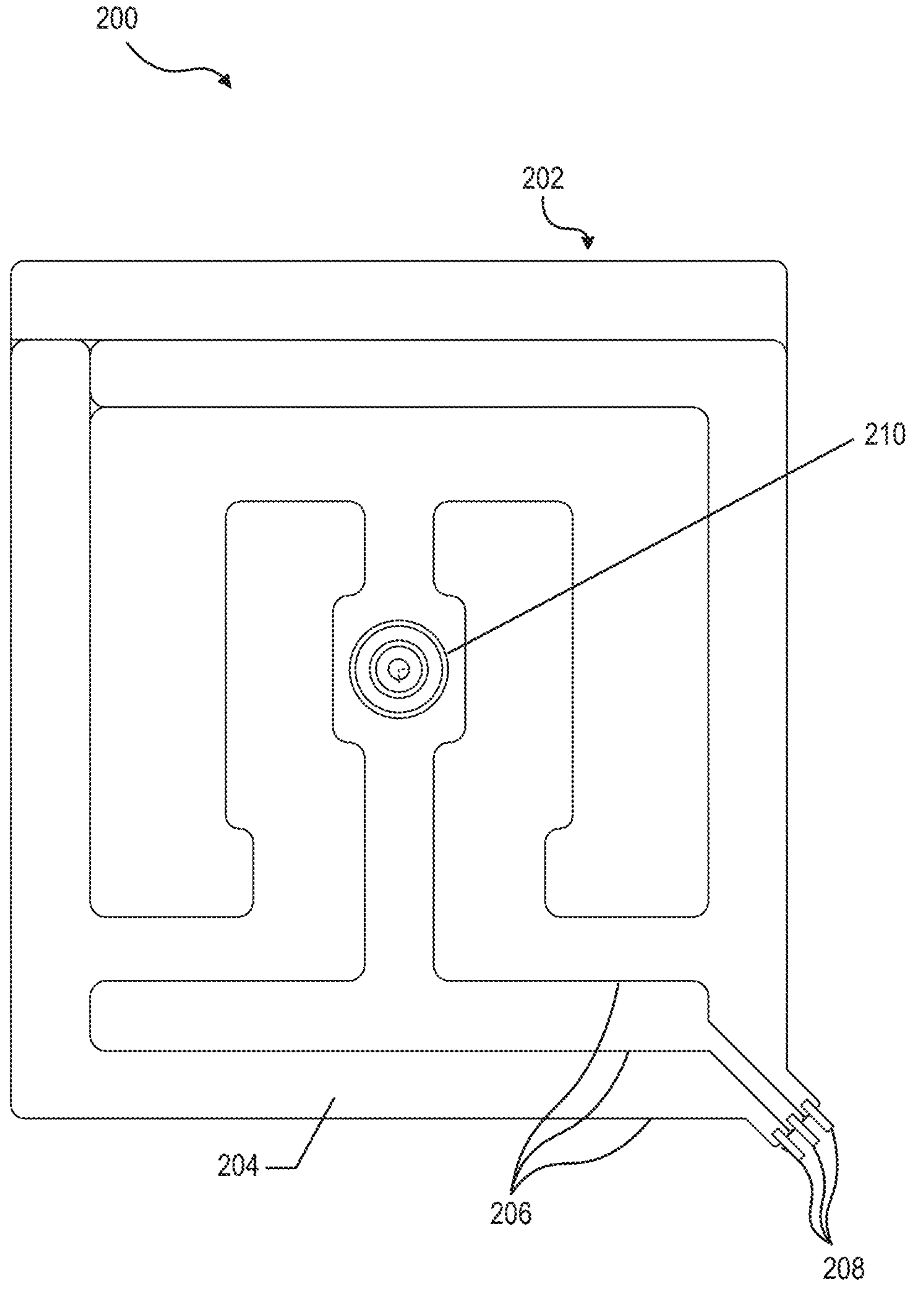
FIGS. 2A-B are top and bottom views, respectively, of a pressure-mitigation device configured in accordance with embodiments of the present technology.
Figure 2B:
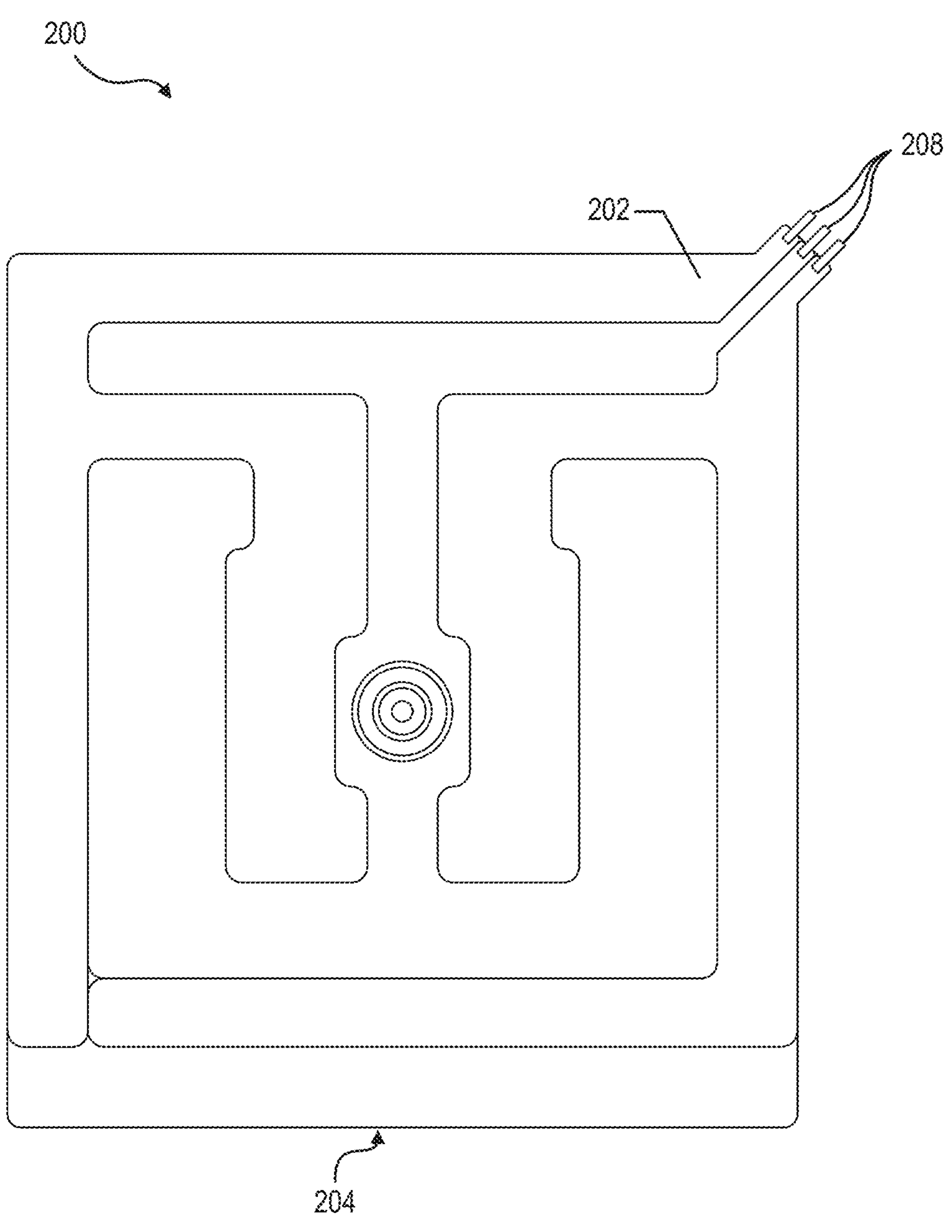

FIGS. 2A-B are top and bottom views, respectively, of a pressure-mitigation device 200 configured in accordance with embodiments of the present technology. The pressure-mitigation device 200 is generally used in conjunction with nonelongated objects that support individuals in a seated or partially erect position. Examples of nonelongated objects include chairs (e.g., office chairs, examination chairs, recliners, and wheelchairs) and the seats included in vehicles and airplanes. Accordingly, the pressure-mitigation device 200 may be positioned atop surfaces that have side supports integrated into the object itself (e.g., the side arms of a recliner or wheelchair). Note, however, that the pressure-mitigation device 200 could likewise be used in conjunction with elongated objects in a manner generally similar to the pressure-mitigation device 100 of FIGS. 1A-B.

In some embodiments, the pressure-mitigation device 200 is secured to a surface using an attachment apparatus. In other embodiments, the attachment apparatus is omitted such that the pressure-mitigation device 200 directly contacts the underlying surface. In such embodiments, the pressure-mitigation device 200 may have a tacky substance deposited along at least a portion of its outer surface that allows it to temporarily adhere to the surface.

The pressure-mitigation device 200 can include various features similar to the features of the pressure-mitigation device 100 described above with respect to FIGS. 1A-B. For example, the pressure-mitigation device 200 may include a first portion 202 (also referred to as a "first layer" or "bottom layer") designed to face the surface, a second portion 204 (also referred to as a "second layer" or "top layer") designed to face the human body supported by the surface, and a plurality of chambers 206 formed via interconnections between the first and second portions 202, 204. In this embodiment, the pressure-mitigation device 200 includes an "M-shaped" chamber intertwined with a backward "J-shaped" chamber and a backward "C-shaped" chamber. Varying the pressure in such an arrangement of chambers 206 has been shown to effectively mitigate the pressure applied by a surface to the gluteal and sacral regions of a human body in a seated position. These chambers may be intertwined to collectively form a square-shaped pattern. Pressure-mitigation devices designed for deployment on the surfaces of non-elongated objects may have substantially quadrilateral-shaped patterns of chambers, while pressure-mitigation devices designed for deployment on the surfaces of elongated objects may have substantially square-shaped patterns of chambers.

As further discussed below, the chambers 206 can be inflated and/or deflated in a predetermined pattern and to predetermined pressure levels. The individual chambers 206 may be inflated to higher pressure levels than the chambers 106 of the pressure-mitigation device 100 described with respect to FIGS. 1A-B because the human body being supported by the pressure-mitigation apparatus 200 is in a seated position, thereby causing more pressure to be applied by the underlying surface than if the human body were in a supine or prone position. Further, unlike the pressure mitigation device 100 of FIGS. 1A-B, the pressure-mitigation device 200 of FIGS. 2A-B does not include side supports. As noted above, side supports may be omitted when the object on which the individual is situated (e.g., seated or reclined) already provides components that will laterally center the human body, as is often the case with nonelongated support surfaces. One example of such a component is the armrests along the side of a chair.

As further described below with respect to FIGS. 6A-C, a controller can control the pressure in each chamber 206 by providing a discrete airflow via one or more corresponding valves 208. Here, the pressure-mitigation apparatus 200 includes three valves 208, and each of the three valves 208 corresponds to a single chamber 206. Other embodiments of the pressure-mitigation apparatus 200 may include fewer than three valves or more than three valves, and each valve can be associated with one or more chambers to control inflation/deflation of those chamber(s). A single valve could be in fluid communication with two or more chambers. Further, a single chamber could be in fluid communication with two or more valves (e.g., one valve for inflation and another valve for deflation).

Figure 3:
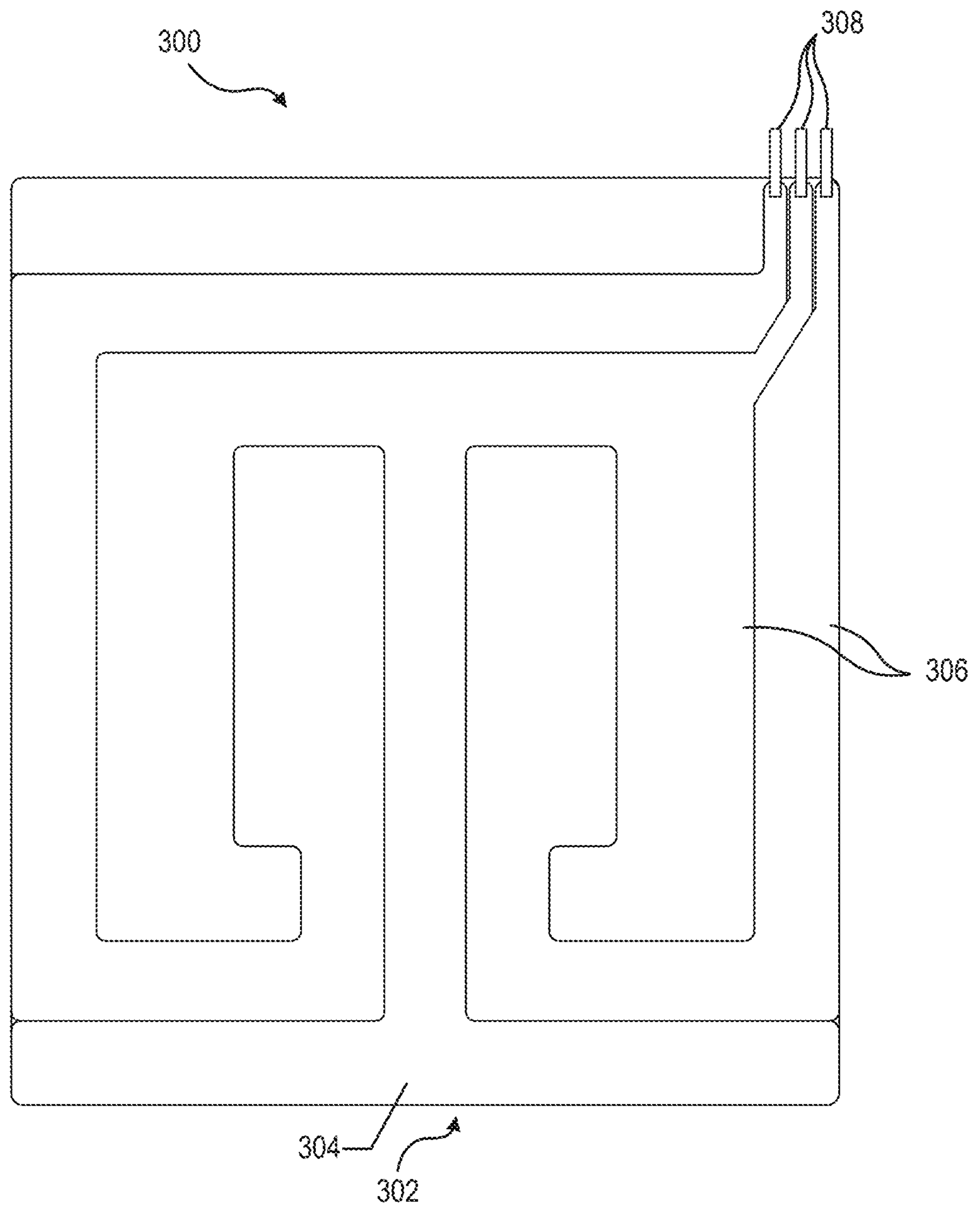
FIG. 3 is a top view of a pressure-mitigation device for relieving pressure on an anatomical region applied by a wheelchair in accordance with embodiments of the present technology.

FIG. 3 is a top view of a pressure-mitigation device 300 for relieving pressure on an anatomical region applied by a wheelchair in accordance with embodiments of the present technology. The pressure-mitigation device 300 can include features similar to the features of the pressure-mitigation device 200 of FIGS. 2A-B and the pressure-mitigation device 100 of FIGS. 1A-B described above. For example, the pressure-mitigation device 300 can include a first portion 302 (also referred to as a "first layer" or "bottom layer") designed to face the seat of the wheelchair, a second portion 304 (also referred to as a "second layer" or "top layer") designed to face the human body supported by the seat of the wheelchair, a series of chambers 306 formed by interconnections between the first and second portions 302, 304, and multiple valves 308 that control the flow of fluid into and/or out of the chambers 306. As can be seen in FIG. 3, the chambers 306 may be arranged similar to those shown in FIGS. 2A-B. Here, however, the pressure-mitigation device 300 is designed such that the valves 308 will be located near the backrest of the wheelchair. Such a design may allow the tubing connected to the valves 308 to be routed through a gap near, beneath, or in the backrest.

In some embodiments the first portion 302 is directly adjacent to the seat of the wheelchair, while in other embodiments the first portion 302 is directly adjacent to an attachment apparatus. As shown in FIG. 3, the pressure-mitigation device 300 may include an "M-shaped" chamber intertwined with a "U-shaped" chamber and a "C-shaped" chamber, which are inflated and deflated in accordance with a predetermined pattern to mitigate the pressure applied to the sacral region of a human body in a sitting position on the seat of a wheelchair. These chambers may be intertwined to collectively form a square-shaped pattern.

Figure 4:
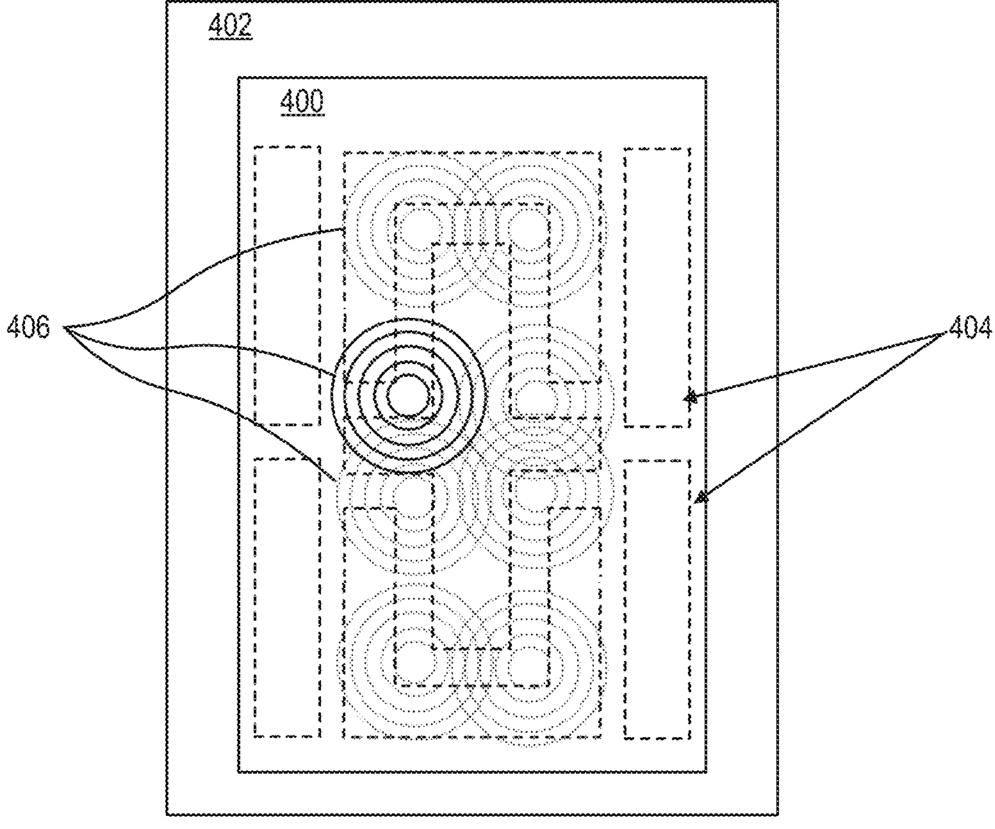
FIG. 4 is a partially schematic top view of a pressure-mitigation device illustrating how a pressure gradient can be created by varying pressure distributions to avoid ischemia in a mobility-impaired patient in accordance with embodiments of the present technology.

FIG. 4 is a partially schematic top view of a pressure-mitigation device 400 illustrating how a pressure gradient can be created by varying pressure distributions to avoid ischemia in a mobility-impaired patient in accordance with embodiments of the present technology. When a human body is supported by a surface 402 for an extended duration, pressure injuries may form in the tissue overlaying bony prominences, such as the skin overlying the sacrum, coccyx, heels, or hips. Generally, these bony prominences represent the locations at which the most pressure is applied by the surface 402 and, therefore, may be referred to as the "main pressure points" along the surface of the human body.

To prevent the formation of pressure injuries, healthy individuals periodically make minor positional adjustments (also known as "micro-adjustments") to shift the location of the main pressure point. However, individuals having impaired mobility often cannot make these micro-adjustments by themselves. Mobility impairment may be due to physical injury (e.g., a traumatic injury or a progressive injury), movement limitations (e.g., within a vehicle, on an aircraft, or in restraints), medical procedures (e.g., those requiring anesthesia), and/or other conditions that limit natural movement. For these mobility-impaired individuals, the pressure-mitigation device 400 can be used to shift the location of the main pressure point(s) on their behalf. That is, the pressure mitigation device 400 can create moving pressure gradients to avoid sustained, localized vascular compression and enhance tissue perfusion.

The pressure-mitigation device 400 can include a series of chambers 404 whose pressure can be individually varied. The chambers 404 may be formed by interconnections between the top and bottom layers of the pressure-mitigation device 400. The top layer may be comprised of a first material (e.g., a permeable, non-irritating material) configured for direct contact with a human body, while the bottom layer may be comprised of a second material (e.g., a non-permeable, gripping material) configured for direct contact with the surface 402. Generally, the first material is permeable to gasses (e.g., air) and/or liquids (e.g., water and sweat) to prevent buildup of fluids that may irritate the skin. Meanwhile, the second material may not be permeable to gasses or liquids to prevent soilage of the underlying object. Accordingly, air discharged into the chambers 404 may be able to slowly escape through the first material (e.g., naturally or via perforations) but not the second material, while liquids may be able to penetrate the first material (e.g., naturally or via perforations) but not the second material. Note, however, that the first material is generally be selected such that the top layer does not actually become saturated with liquid to reduce the likelihood of irritation. Instead, the top layer may allow liquid to pass therethrough into the cavities, from which the liquid can be subsequently discharged (e.g., as part of a cleaning process). The top layer and/or the bottom layer can be comprised of more than one material, such as a coated fabric or a stack of interconnected materials.

The pressure-mitigation device 400 may be designed such that inflation of at least some of the chambers 404 causes air to be continuously exchanged across the surface of the human body. Said another way, simultaneous inflation of at least some of the chambers 404 may provide a desiccating effect to inhibit generation and/or collection of moisture along the skin in a given anatomical region. In some embodiments, the pressure-mitigation device 400 is able to maintain airflow through the use of a porous material. For example, the top layer may be comprised of a biocompatible material through which air can flow (e.g., naturally or via perforations). In other embodiments, the pressure-mitigation device 400 is able to maintain airflow without the use of a porous material. For example, airflows can be created and/or permitted simply through varied pressurization of the chambers 404. This represents a new approach to microclimate management that is enabled by simultaneous inflation and deflation of the chambers 404. At a high level, each void formed beneath a human body due to deflation of at least one chamber can be thought of as a microclimate that cools and desiccates the corresponding portion of the anatomical region. Heat and humidity can lead to injury (e.g., further development of ulcers), so the cooling and desiccating effects may present some injuries due to inhabitation of moisture generation/collection along the skin in the anatomical region.

As discussed below with respect to FIG. 15, a pump (also referred to as a "pressure device") can be fluidically coupled to each chamber 404 (e.g., via a corresponding valve), while a controller can control the flow of fluid generated by the pump into each chamber 404 on an individual basis in accordance with a predetermined pattern. The controller can operate the series of chambers 404 in several different ways.

In some embodiments, the chambers 404 have a naturally deflated state, and the controller causes the pump to inflate at least one of the chambers 404 to shift the main pressure point along the anatomy of the user. For example, the pump may inflate at least one chamber 404 located directly beneath an anatomical region to momentarily apply contact pressure to that anatomical region and relieve contact pressure on the surrounding anatomical regions adjacent to the deflated chamber(s) 404. The controller may cause the pump to inflate two or more chambers 404 adjacent to an anatomical region to create a void beneath the anatomical region to shift the main pressure point at least momentarily away from the anatomical region.

In other embodiments, the chambers 404 have a naturally inflated state, and the controller causes the pump to deflate at least one of the chambers 404 to shift the main pressure point along the anatomy of the user. For example, the pump may deflate at least one chamber 404 located directly beneath an anatomical region, thereby forming a void beneath the anatomical region to momentarily relieve the contact pressure on the anatomical region.

Whether configured in a naturally deflated state or a naturally inflated state, the continuous or intermittent alteration of the inflation levels of the individual chambers 404 moves the location of the main pressure point across different portions of the human body. As shown in FIG. 4, for example, inflating and/or deflating the chambers 404 creates temporary contact regions 406 that move across the pressure-mitigation device 400 in a predetermined pattern, and thereby changing the location of the main pressure point(s) on the human body for finite intervals of time. Thus, the pressure-mitigation device 400 can simulate the micro-adjustments made by healthy individuals to relieve stagnant pressure applied by the surface 402.

The series of chambers 404 may be arranged in an anatomy-specific pattern so that when the pressure of one or more chambers is altered, the contact pressure on a specific anatomical region of the human body is relieved (e.g., by shifting the main pressure point elsewhere). As an example, the main pressure point may be moved between eight different locations corresponding to the eight temporary contact regions 406 as shown in FIG. 4. In some embodiments the main pressure point shifts between these locations in a predictable manner (e.g., in a clockwise or counter-clockwise pattern), while in other embodiments the main pressure point shifts between these locations in an unpredictable manner (e.g., in accordance with a random pattern, a semi-random pattern, and/or detected pressure levels). Those skilled in the art will recognize that the quantity and position of these temporary contact regions 406 may vary based on the arrangement of the chambers 404, the number of the chambers 404, the anatomical region supported by the pressure-mitigation device 400, the characteristics of the human body supported by the pressure mitigation device 400, and/or the condition of the user (e.g., whether the user is completely immobilized, partially immobilized, etc.).

As discussed above, the pressure-mitigation device 400 may not include side supports if the condition of the user (also referred to as the "patient" or "subject") would not benefit from the positioning assistance provided by the side supports. For example, side supports can be omitted when the patient is medically immobilized (e.g., under anesthesia, in a medically induced coma, etc.) and/or physically restrained on the underlying surface 402 (e.g., by rails along the side of a bed, arm rests on the side of a chair, restraints limiting movement of the patient, casts, etc.).

Figure 5A:
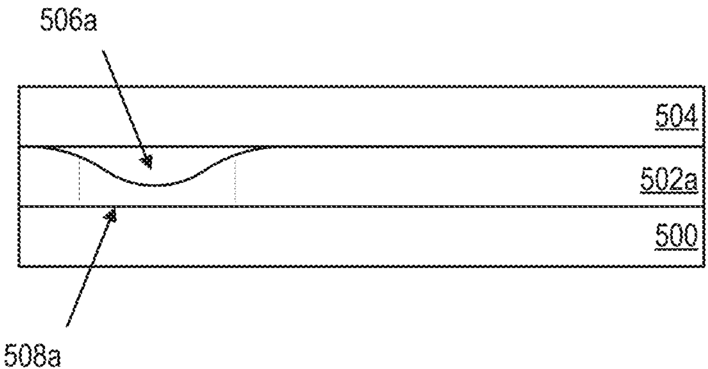
FIG. 5A is a partially schematic side view of a pressure-mitigation device for relieving pressure on a specific anatomical region by deflating chamber(s) in accordance with embodiments of the present technology.

FIG. 5A is a partially schematic side view of a pressure-mitigation device 502*a* for relieving pressure on a specific anatomical region by deflating chamber(s) in accordance with embodiments of the present technology. The pressure-mitigation device 502*a* can be positioned between the surface of an object 500 and a human body 504. Examples of objects 500 include beds, tables, and chairs. To relieve the pressure on a specific anatomical region of the human body 504, at least one chamber 508*a* of multiple chambers (collectively referred to as "chambers 508") proximate to the specific anatomical region is at least partially deflated to create a void 506*a* beneath the specific anatomical region. In such embodiments, the remaining chambers 508 may remain inflated. Thus, the pressure-mitigation device 502*a* may sequentially deflate chambers (or arrangements of multiple chambers) to relieve the pressure applied to the human body 504 by the surface of the object 500.

Figure 5B:
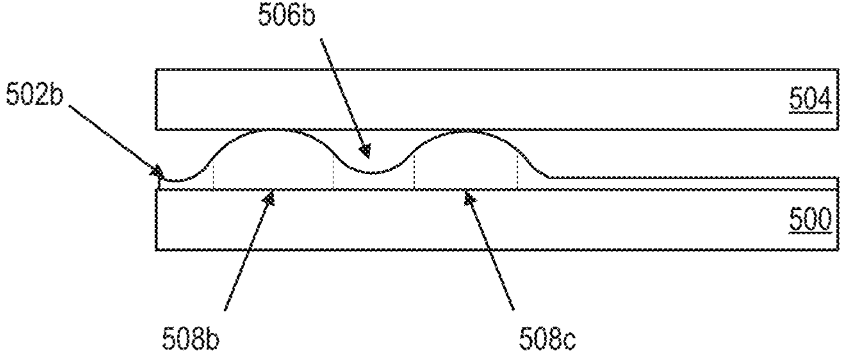
FIG. 5B is a partially schematic side view of a pressure-mitigation device for relieving pressure on a specific anatomical region by inflating chamber(s) in accordance with embodiments of the present technology.

FIG. 5B is a partially schematic side view of a pressure-mitigation device 502*b* for relieving pressure on a specific anatomical region by inflating chamber(s) in accordance with embodiments of the present technology. For example, to relieve the pressure on a specific anatomical region of the human body 504, the pressure-mitigation device 502*b* can inflate two chambers 508*b* and 508*c* disposed directly adjacent to the specific anatomical region to create a void 506*b* beneath the specific anatomical region. In such embodiments, the remaining chambers may remain partially or entirely deflated. Thus, the pressure-mitigation device 502*b* may sequentially inflate a chamber (or arrangements of multiple chambers) to relieve the pressure applied to the human body 504 by the surface of the object 500.

The pressure-mitigation devices 502*a*, 502*b* of FIGS. 5A-B are shown to be in direct contact with the contact surface 500. However, in some embodiments, an attachment apparatus is positioned between the pressure-mitigation devices 502*a*, 502*b* and the contact surface 500.

In some embodiments, the pressure-mitigation devices 502*a*, 502*b* of FIGS. 5A-B have the same configuration of chambers 508, and can operate in both a normally inflated state (described with respect to FIG. 5A) and a normally deflated state (described with respect to FIG. 5B) based on the selection of an operator (e.g., the user or some other person, such as a medical professional). For example, the operator can use a controller to select a normally deflated mode such that the pressure-mitigation device operates as described with respect to FIG. 5B, and then change the mode of operation to a normally inflated mode such that the pressure-mitigation device operates as described with respect to FIG. 5A. Thus, the pressure-mitigation devices described herein can shift the location of the main pressure point by controllably inflating chambers, controllably deflating chambers, or a combination thereof.

Overview of Controller Devices

Figure 6A:
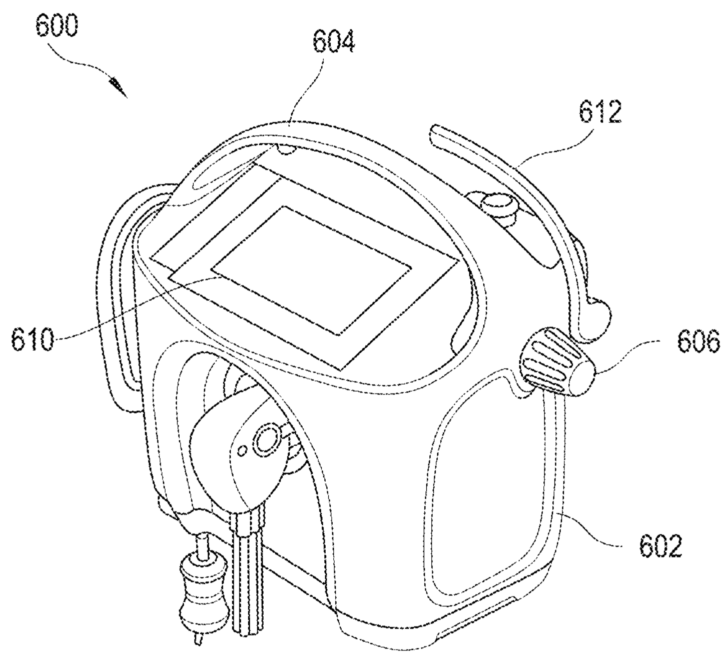
FIGS. 6A-C are isometric, front, and back views, respectively, of a controller device (also referred to as a "controller") that is responsible for controlling inflation and/or deflation of the chambers of a pressure-mitigation device in accordance with embodiments of the present technology.
Figure 6B:
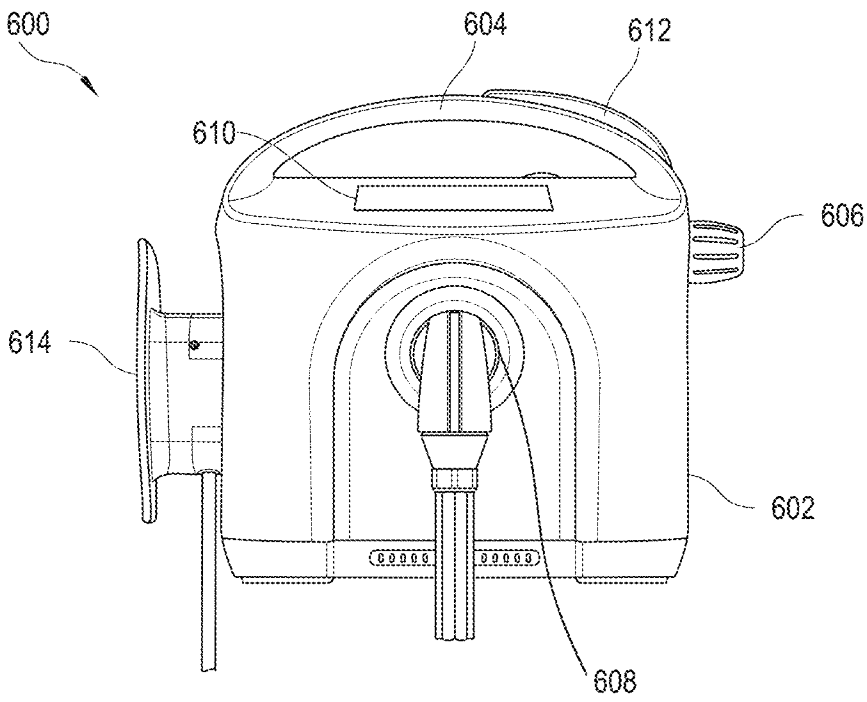
Figure 6C:
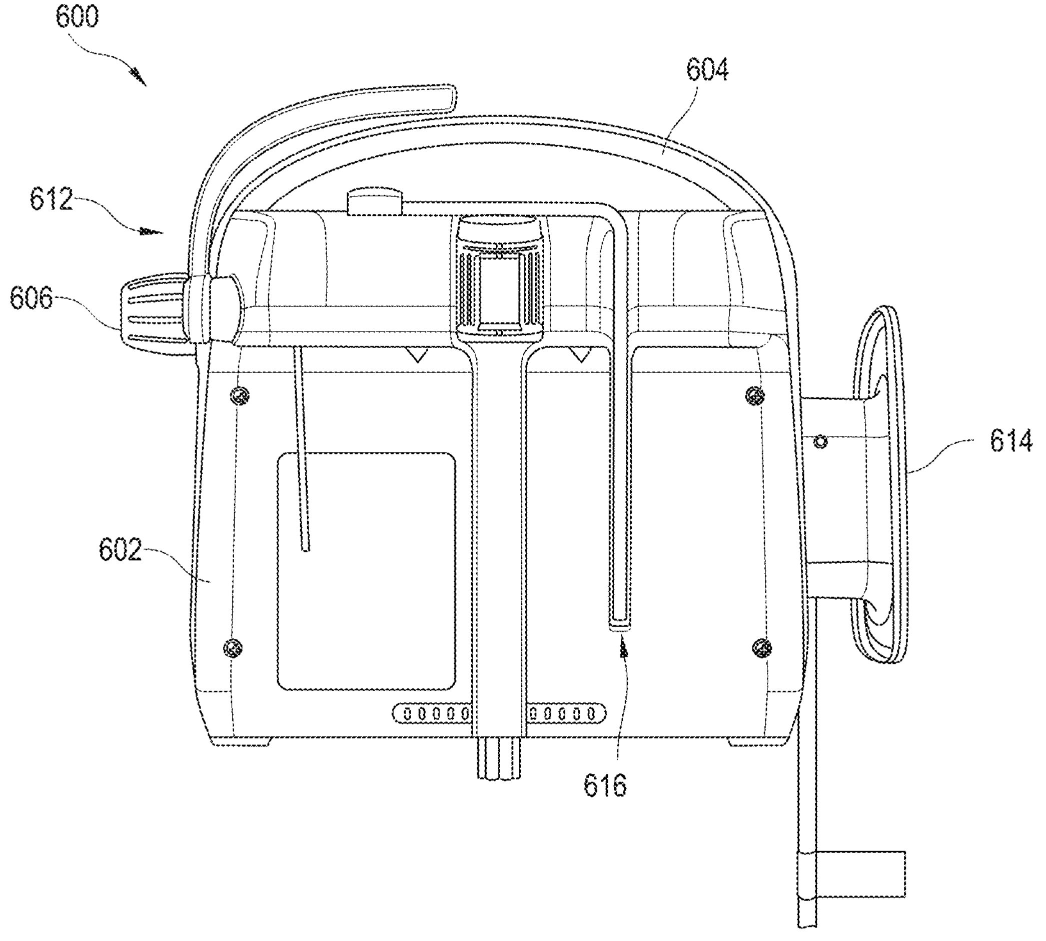

FIGS. 6A-C are isometric, front, and back views, respectively, of a controller device 600 (also referred to as a "controller") that is responsible for controlling inflation and/or deflation of the chambers of a pressure-mitigation device in accordance with embodiments of the present technology. For example, the controller 600 can be coupled to the pressure-mitigation devices 100, 200, 300 described above with respect to FIGS. 1A-3 to control the pressure within the chambers 106, 206, 306. The controller 600 can manage the pressure in each chamber of a pressure-mitigation device by controllably driving one or more pumps. In some embodiments, a single pump is fluidically connected to all the chambers such that the pump is responsible for directing fluid flow to and/or from multiple chambers. In other embodiments, the controller 600 is coupled to two or more pumps, each of which can be fluidically coupled to a single chamber to drive inflation/deflation of that chamber. In other embodiments, the controller 600 is coupled to at least one pump that is fluidically coupled to two or more chambers and/or at least one pump that is fluidically coupled to a single chamber. The pump(s) may reside within the housing of the controller 600 such that the system is easily transportable. Alternatively, the pump(s) may reside in a housing separate from the controller 600.

As shown in FIGS. 6A-C, the controller 600 can include a housing 602 in which internal components (e.g., those described below with respect to FIG. 7) reside and a handle 604 that is connected to the housing 602. In some embodiments the handle 604 is fixedly secured to the housing 602 in a predetermined orientation, while in other embodiments the handle 604 is pivotably secured to the housing 602. For example, the handle 604 may be rotatable about a hinge connected to the housing 602 between multiple positions. The hinge may be one of a pair of hinges connected to the housing 602 along opposing lateral sides. The handle 604 enables the controller 600 to be readily transported, for example, from a storage location to a deployment location (e.g., proximate a user positioned on a surface). Moreover, the handle 604 could be used to releasably attach the controller 600 to a structure. For example, the handle could be hooked on an intravenous (IV) pole (also referred to as an "IV stand" or "infusion stand").

In some embodiments, the controller 600 includes a retention mechanism 614 that is attached to, or integrated within, the housing 602. Cords (e.g., electrical cords), tubes, and/or other elongated structures associated with the system can be wrapped around or otherwise supported by the retention mechanism 614. Thus, the retention mechanism 614 may provide strain relief and retention of an electrical cord (also referred to as a "power cord"). In some embodiments, the retention mechanism 614 includes a flexible flange that can retain the plug of the electrical cord.

As further shown in FIGS. 6A-C, the controller 600 may include a connection mechanism 612 that allows the housing 602 to be securely, yet releasably, attached to a structure. Examples of structures include IV poles, mobile workstations (also referred to as "mobile carts"), bedframes, rails, handles (e.g., of wheelchairs), and tables. The connection mechanism 612 may be used instead of, or in addition to, the handle 604 for mounting the controller 600 to the structure. In the illustrated embodiment, the connection mechanism 612 is a mounting hook that allows for single-hand operation and is adjustable to allow for attachment to mounting surfaces with various thicknesses. In some embodiments, the controller 600 includes an IV pole clamp 616 that eases attachment of the controller 600 to IV poles. The IV pole clamp 616 may be designed to enable quick securement, and the IV pole clamp 616 can be self-centering with the use of a single activation mechanism (e.g., knob or button).

In some embodiments, the housing 602 includes one or more input components 606 for providing instructions to the controller 600. The input component(s) 606 may include knobs (e.g., as shown in FIGS. 6A-C), dials, buttons, levers, and/or other actuation mechanisms. An operator can interact with the input component(s) 606 to alter the airflow provided to the pressure-mitigation device, discharge air from the pressure-mitigation device, or disconnect the controller 600 from the pressure-mitigation device (e.g., by disconnecting the controller 600 from tubing connected between the controller 600 and pressure-mitigation device).

As further discussed below, the controller 600 can be configured to inflate and/or deflate the chambers of a pressure-mitigation device in a predetermined pattern by managing the flow of fluid (e.g., air) produced by one or more pumps. In some embodiments the pump(s) reside in the housing 602 of the controller 600, while in other embodiments the controller 600 is fluidically connected to the pump(s). For example, the housing 602 may include a first fluid interface through which fluid is received from the pump(s) and a second fluid interface through which fluid is directed to the pressure-mitigation device. Multi-channel tubing may be connected to either of these fluid interfaces. For example, multi-channel tubing may be connected between the first fluid interface of the controller 600 and multiple pumps. As another example, multi-channel tubing may be connected between the second fluid interface of the controller 600 and multiple valves of the pressure-mitigation device. Here, the controller 600 includes a fluid interface 608 designed to interface with multi-channel tubing. In some embodiments the multi-channel tubing permits unidirectional fluid flow, while in other embodiments the multi-channel tubing permits bidirectional fluid flow. Thus, fluid returning from the pressure-mitigation device (e.g., as part of a discharge process) may travel back to the controller 600 through the second fluid interface. By controlling the exhaust of fluid returning from the pressure-mitigation device, the controller 600 can actively manage the noise created during use.

By monitoring the connection with the fluid interface 608, the controller 600 may be able to detect which type of pressure-mitigation device has been connected. Each type of pressure-mitigation device may include a different type of connector. For example, a pressure-mitigation device designed for elongated objects (e.g., the pressure-mitigation device 100 of FIGS. 1A-B) may include a first arrangement of magnets in its connector, while a pressure-mitigation device designed for non-elongated objects (e.g., the pressure-mitigation device of FIGS. 2A-B) may include a second arrangement of magnets in its connector. The controller 600 may include one or more sensors arranged near the fluid interface 608 that are able to detect whether magnets are located within a specified proximity. The controller 600 may automatically determine, based on which magnets have been detected by the sensor(s), which type of pressure-mitigation device is connected.

Pressure-mitigation devices may have different geometries, layouts, and/or dimensions suitable for various positions (e.g., supine, prone, sitting), various supporting objects (e.g., wheelchair, bed, recliner, surgical table), and/or various user characteristics (e.g., weight, size, ailment), and the controller 600 can be configured to automatically detect the type of pressure-mitigation device connected thereto. In some embodiments, the automatic detection is performed using other suitable identification mechanisms, such as the controller 600 reading a radio-frequency identification (RFID) tag or barcode on the pressure-mitigation device. Alternatively, the controller 600 may permit the operator to specify the type of pressure-mitigation device connected thereto. For example, the operator may be able to select, using an input component (e.g., input component 606), a type of pressure-mitigation device via a display 610. The controller 600 can be configured to dynamically alter the pattern for inflating and/or deflating chambers based on which type of pressure-mitigation device is connected.

As shown in FIGS. 6A-B, the controller 600 may include a display 610 for displaying information related to the pressure-mitigation device, the pattern of inflations/deflations, the patient, etc. For example, the display 610 may present an interface that specifies which type of pressure-mitigation device (e.g., the pressure-mitigation apparatuses 100, 200, 300 of FIGS. 1A-3) is connected to the controller 600. Other display technologies could also be used to convey information to an operator of the controller 600. In some embodiments, the controller 600 includes a series of lights (e.g., light-emitting diodes) that are representative of different statuses to provide visual alerts to the operator or the user. For example, a status light may provide a green visual indication if the controller 600 is presently providing therapy, a yellow visual indication if the controller 600 has been paused (i.e., is in a pause mode), a red visual indication if the controller 600 has experienced an issue (e.g., non-compliance of patient, patient not detected) or requires maintenance (i.e., is in an alert mode), etc. These visual indications may dim upon the conclusion of a specified period of time or upon determining that the status has changed (e.g., the pause mode is no longer active).

In some embodiments, the controller 600 includes a rapid deflate function that allows an operator to rapidly deflate the pressure-mitigation device. The rapid deflate function may be designed such that the entire pressure-mitigation device is deflated or a portion (e.g., the side supports) of the pressure-mitigation device is deflated. This is a software solution that can be activated via the display 610 (e.g., when configured as a touch-enabled interface) and/or input components (e.g., tactile actuators such as buttons, switches, etc.) on the controller 600. This rapid deflation, in particular the deflation of the side supports, is expected to be beneficial to operators when there is a need for quick access to the user, such as to provide cardiopulmonary resuscitation (CPR).

Figure 7:
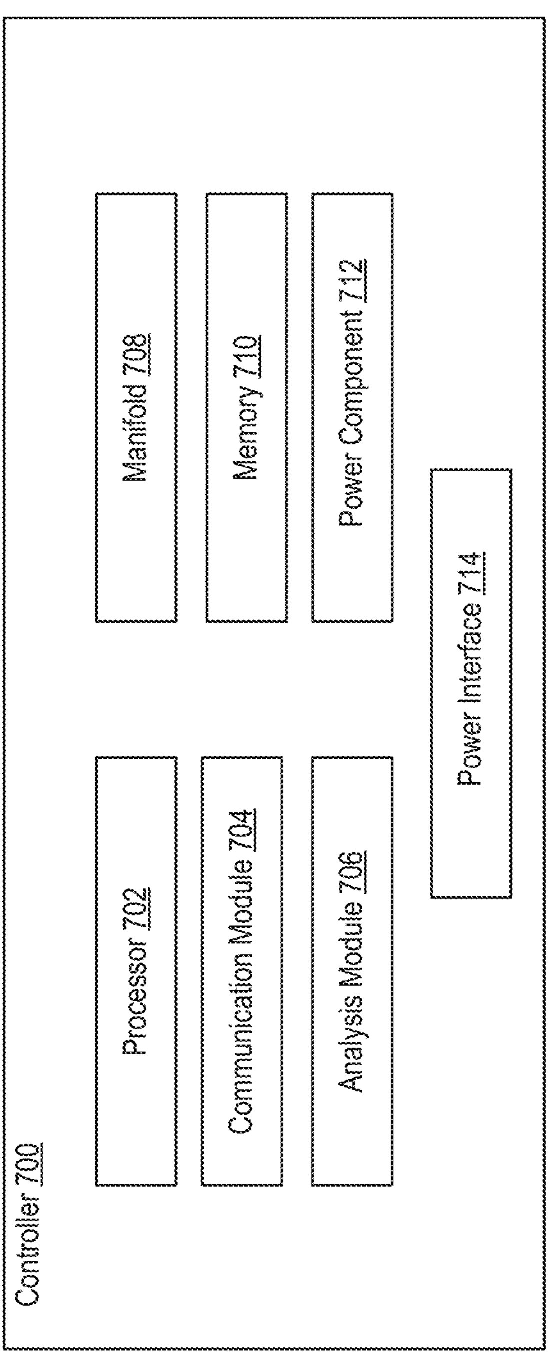
FIG. 7 is a block diagram illustrating components of a controller in accordance with embodiments of the present technology.

FIG. 7 is a block diagram illustrating components of a controller 700 in accordance with embodiments of the present technology. The controller 700 can include a processor 702, communication module 704, analysis module 706, manifold 708, memory 710, and/or power component 712 that is electrically coupled to a power interface 714. These components may reside within a housing (also referred to as a "structural body"), such as the housing 602 described above with respect to FIGS. 6A-C. In some embodiments, the controller 700 is incorporated into other component(s) of a pressure-mitigation system. For example, some components of the controller 700 may be incorporated into a computing device (e.g., a mobile phone or a mobile workstation) that is remotely coupled to a pressure-mitigation device. Embodiments of the controller 700 can include any subset of the components shown in FIG. 7, as well as additional components not illustrated here. For example, some embodiments of the controller 700 include a physical data interface through which data can be transmitted to another computing device. Examples of physical data interfaces include Ethernet ports, Universal Serial Bus (USB) ports, and proprietary ports.

The controller 700 may be connected to a pressure-mitigation device that includes a series of chambers whose pressure can be individually varied. When the pressure-mitigation device is placed between a human body and the surface of an object, the controller 700 can cause the pressure on an anatomical region of the human body to be varied by controllably inflating chamber(s), deflating chamber(s), or any combination thereof. Such action can be accomplished by the manifold 708, which controls the flow of fluid to the series of chambers of the pressure-mitigation device. The manifold 708 is further described with respect to FIGS. 8-9.

As further discussed below, transducers mounted in the manifold 708 can generate an electrical signal based on the pressure detected in each chamber of the pressure-mitigation device. Generally, each chamber is associated with a different fluid channel and a different transducer. Accordingly, if the manifold 708 is designed to facilitate the flow of fluid to a four-chamber pressure-mitigation device, the manifold 708 may include four fluid channels and four transducers. In some embodiments, the manifold 708 includes fewer than four fluid channels and/or transducers or more than four fluid channels and/or transducers. Pressure data representative of the values of the electrical signals generated by the transducers can be stored, at least temporarily, in the memory 710. As further discussed below, the manifold 708 may be driven based on a clock signal generated by a clock module (not shown). For example, the processor 702 may be configured to generate signals for driving valves in the manifold 708 (or driving integrated circuits in communication with the valves) based on a comparison of the clock signal to a programmed pattern that indicates when the chambers of the pressure-mitigation device should be inflated or deflated.

In some embodiments, the processor 702 processes the pressure data prior to examination by the analysis module 706. For example, the processor 702 may apply algorithms designed for temporal aligning, artifact removal, and the like. In other embodiments, the analysis module 706 is designed to analyze the pressure data in its unprocessed (i.e., raw) form. As further discussed below, the processor 702 may forward at least some of the pressure data, in either its processed or unprocessed form, to the communication module 704 for transmittal to another computing device for analysis. By examining the pressure data in conjunction with flow data representative of the fluid flowing into the controller 700 from the pump(s), the analysis module 706 can control how the chambers of the pressure-mitigation device are inflated and/or deflated. For example, the analysis module 706 may be responsible for separately controlling the set point for fluid flowing into each chamber such that the pressures of the chambers match a predetermined pattern.

By examining the pressure data, the analysis module 706 may also be able to sense movements of the human body under which the pressure-mitigation device is positioned. These movements may be caused by the patient, another individual (e.g., a caregiver or an operator of the controller 700), or the underlying surface. The analysis module 706 may apply algorithm(s) to the data representative of these movements (also referred to as "movement data" or "motion data") to identify repetitive movements and/or random movements to better understand the health state of the patient. For example, the analysis module 706 may be able to produce a coverage metric indicative of the amount of time that the human body is properly positioned on the pressure-mitigation device. As further discussed below, the controller 700 (or another computing device) may be able to establish whether the pressure-mitigation device has been properly deployed/operated based on the coverage metric. As another example, the analysis module 706 may be able to establish the respiration rate, heart rate, or another vital measurement based on the movements of a patient. Generally, the movement data is derived from the pressure data. That is, the analysis module 706 may be able to infer movements of the human body by analyzing the pressure of the chambers of the pressure-mitigation device in conjunction with the rate at which fluid is being delivered to those chambers. Consequently, the pressure-mitigation device may not actually include any sensors for measuring movement, such as accelerometers, tilt sensors, or gyroscopes.

The analysis module 706 may respond in several ways after examining the pressure data. For example, the analysis module 706 may generate a notification (e.g., an alert) to be transmitted to another computing device by the communication module 704. The other computing device may be associated with a healthcare professional (e.g., a physician or a nurse), a family member of the patient, or some other entity (e.g., a researcher or an insurer). The communication module 704 may be, for example, wireless communication circuitry designed to establish communication channels with other computing devices. Examples of wireless communication circuitry include integrated circuits (also referred to as "chips") configured for Bluetooth, Wi-Fi, NFC, and the like. As another example, the analysis module 706 may cause the pressure data (or analyses of such data) to be integrated with the electronic health record of the patient. Generally, the electronic health record is maintained in a storage medium accessible to the communication module 704 across a network.

The controller 700 may include a power component 712 that is able to provide to the other components residing within the housing, as necessary. Examples of power components include rechargeable lithium-ion (Li-Ion) batteries, rechargeable nickel-metal hydride (NiMH) batteries, rechargeable nickel-cadmium (NiCad) batteries, etc. In some embodiments, the controller 700 does not include a power component, and thus must receive power from an external source. In such embodiments, a cable designed to facilitate the transmission of power (e.g., via a physical connection of electrical contacts) may be connected between the power interface 714 of the controller 700 and the external source. The external source may be, for example, an alternating current (AC) power socket or another electronic device.

Figure 8:
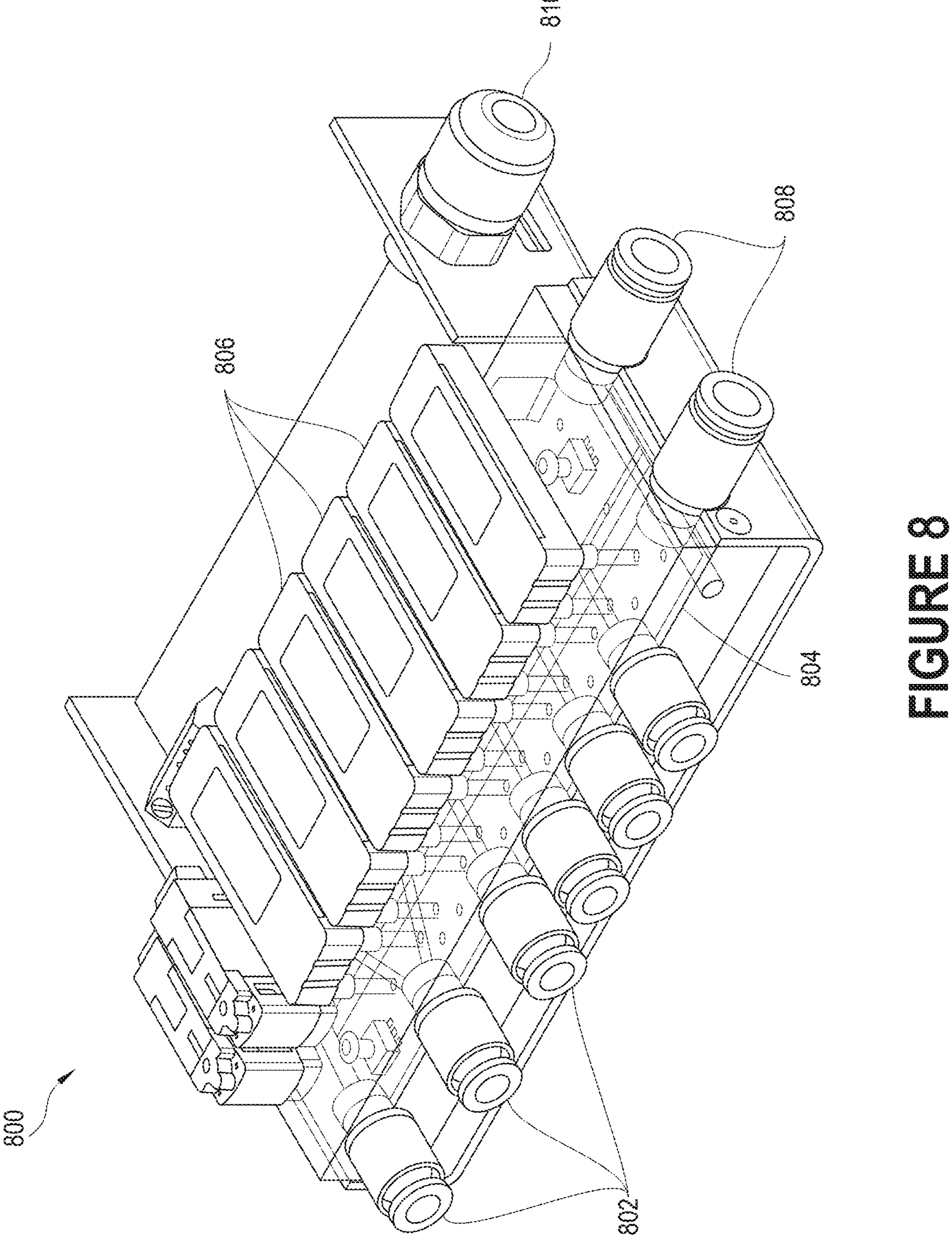
FIG. 8 is an isometric view of a manifold for controlling the flow of fluid (e.g., air) to the chambers of a pressure-mitigation device in accordance with embodiments of the present technology.

FIG. 8 is an isometric view of a manifold 800 for controlling the flow of fluid (e.g., air) to the chambers of a pressure-mitigation device in accordance with embodiments of the present technology. As discussed above, a controller can be configured to inflate and/or deflate the chambers of a pressure-mitigation device to create a pressure gradient that moves the main point of pressure applied by an object across the surface of a human body situated on the pressure-mitigation device. To accomplish this, the manifold 800 can guide fluid to the chambers through a series of valves 802. In some embodiments, each valve 802 corresponds to a separate chamber of the pressure-mitigation device. In some embodiments, at least one valve 802 corresponds to multiple chambers of the pressure-mitigation device. In some embodiments, at least one valve 802 is not used during operation. For example, if the pressure-mitigation device includes four chambers, multi-channel tubing may be connected between the pressure-mitigation device and four valves 802 of the manifold 800. In such embodiments, the other valves may remain sealed during operation.

Generally, the valves 802 are piezoelectric valves designed to switch from one state (e.g., an open state) to another state (e.g., a closed state) in response to an application of voltage. Each piezoelectric valve includes at least one piezoelectric element that acts as an electromechanical transducer. When a voltage is applied to the piezoelectric element, the piezoelectric element is deformed, thereby resulting in mechanical motion (e.g., the opening or closing of a valve). Examples of piezoelectric elements include disc transducers, bender actuators, and piezoelectric stacks.

Piezoelectric valves provide several benefits over other valves, such as linear valves and solenoid-based valves. First, piezoelectric valves do not require holding current to maintain a state. As such, piezoelectric valves generate almost no heat. Second, piezoelectric valves create almost no noise when switching between states, which can be particularly useful in medical settings. Third, piezoelectric valves can be opened and closed in a controlled manner that allows the manifold 800 to precisely approach a desired flow rate without overshoot or undershoot. In contrast, the other valves described above must be in either an open state, in which the valve is completely open, or a closed state, in which the valve is completely closed. Fourth, piezoelectric valves require very little power to operate, so a power component (e.g., power component 712 of FIG. 7) may only need to provide 3-6 watts to the manifold 800 at any given time. While embodiments of the manifold 800 may be described in the context of piezoelectric valves, other types of valves, such as linear valves or solenoid-based valves, could be used instead of, or in addition to, piezoelectric valves.

In some embodiments, the manifold 800 includes one or more transducers 806 and a circuit board 804 that includes one or more integrated circuits (also referred to as "chips") for managing communication with the valves 802 and the transducer(s) 806. Because these local chip(s) reside within the manifold 800 itself, the valves 802 can be digitally controlled in a precise manner. The local chip(s) may be connected to other components of the controller. For example, the local chip(s) may be connected to other components housed within the controller, such as processors (e.g., processor 702 of FIG. 7) and clock modules. The transducer(s) 806, meanwhile, can generate an electrical signal based on the pressure of each chamber of the pressure-mitigation device. Generally, each chamber is associated with a different valve 802 and a different transducer 806. Here, for example, the manifold includes six valves 802 capable of interfacing with the pressure-mitigation device, and each of these valves may be associated with a corresponding transducer 806. Pressure data representative of the values of the electrical signals generated by the transducer(s) 806 can be provided to other components of the controller for further analysis.

The manifold 800 may also include one or more compressors. In some embodiments each valve 802 of the manifold 800 is fluidically coupled to the same compressor, while in other embodiments each valve 802 of the manifold 800 is fluidically coupled to a different compressor. Each compressor can increase the pressure of fluid by reducing its volume before guiding the fluid to the pressure-mitigation device.

Fluid produced by a pump may initially be received by the manifold 800 through one or more ingress fluid interfaces 808 (or simply "ingress interfaces"). As noted above, in some embodiments, a compressor may then increase pressure of the fluid by reducing its volume. Thereafter, the manifold 800 can controllably guide the fluid into the chambers of a pressure-mitigation device through the valves 802. The flow of fluid into each chamber can be controlled by local chip(s) disposed on the circuit board 804. For example, the local chip(s) can dynamically vary the flow of fluid into each chamber in real time by controllably applying voltages to open/close the valves 802.

In some embodiments, the manifold includes one or more egress fluid interfaces 810 (or simply "egress interfaces"). The egress fluid interface(s) 810 may be designed for high pressure and high flow to permit rapid deflation of the pressure-mitigation device. For example, upon determining that an operator has provided input indicative of a request to deflate the pressure-mitigation device (or a portion thereof), the manifold 800 may allow fluid to travel back though the valve(s) 802 from the pressure-mitigation device and then out through the egress fluid interface(s) 810. Thus, the egress fluid interface(s) 810 may also be referred to as "exhausts" or "outlets." To provide the input, the operator may interact with a mechanical input component (e.g., mechanical input component 606 of FIG. 6A) or a digital input component (e.g., visible on display 610 of FIG. 6A).

Figure 9:
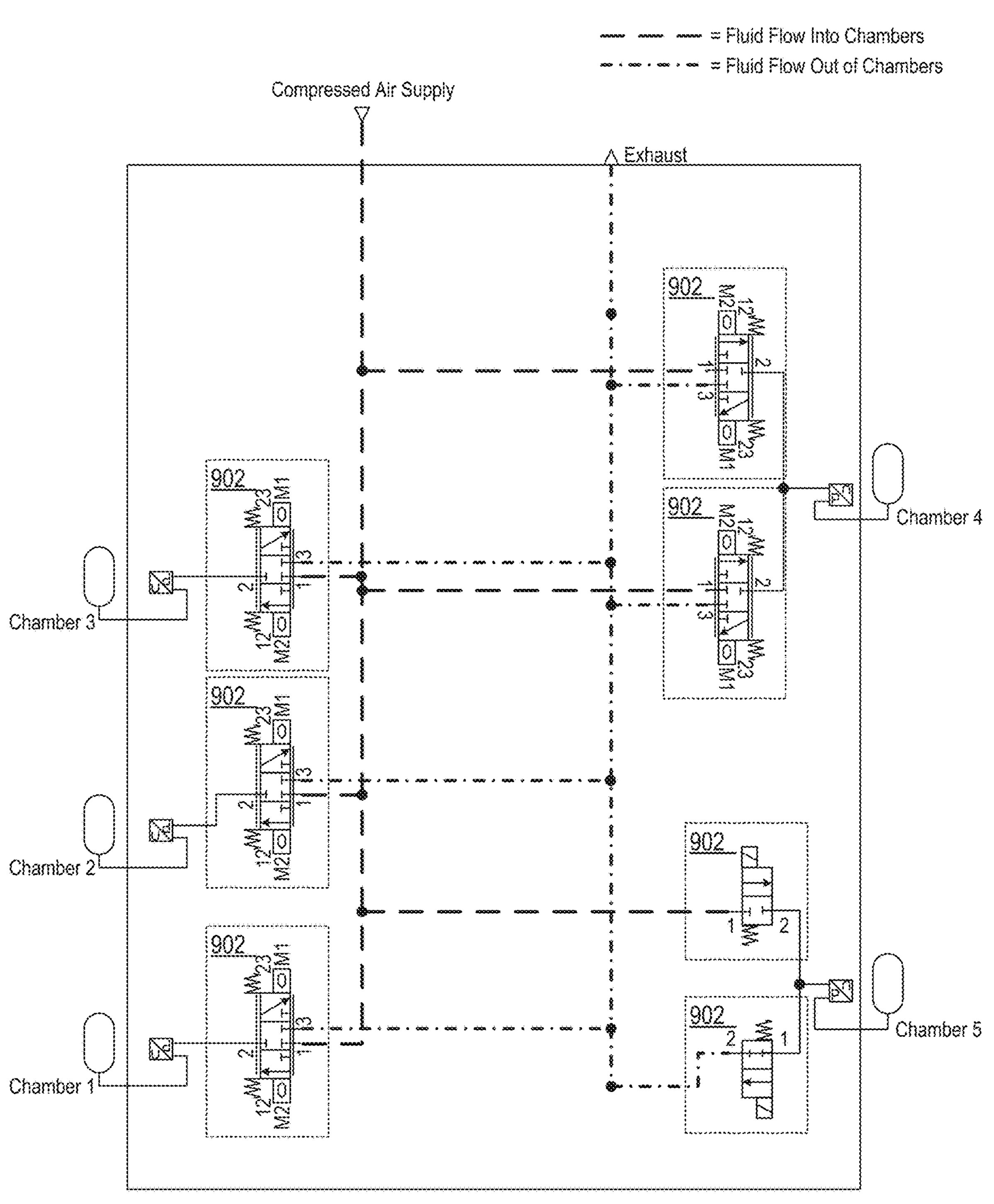
FIG. 9 is a generalized electrical diagram illustrating how the piezoelectric valves of a manifold can separately control the flow of fluid along multiple channels in accordance with embodiments of the present technology.

FIG. 9 is a generalized electrical diagram illustrating how the piezoelectric valves 902 of a manifold can separately control the flow of fluid along multiple channels in accordance with embodiments of the present technology. In FIG. 9, the manifold includes seven piezoelectric valves 902. Other embodiments of the manifold may include fewer than seven valves or more than seven valves. Fluid, such as air, can be guided by the manifold through the piezoelectric valves 902 to the chambers of a pressure-mitigation device. In FIG. 9, the manifold is fluidically connected to a pressure-mitigation device that has five chambers. However, in other embodiments, the manifold may be fluidically connected to a pressure-mitigation device that has fewer than five chambers or more than five chambers.

All of the piezoelectric valves 902 included in the manifold need not necessarily be identical to one another. Piezoelectric valves may be designed for high pressure and low flow, high pressure and high flow, low pressure and low flow, or low pressure and high flow. In some embodiments all of the piezoelectric valves included in the manifold are the same type, while in other embodiments the manifold includes multiple types of piezoelectric valves. For example, piezoelectric valves corresponding to side supports of the pressure-mitigation device may be designed for high pressure and high flow (e.g., to allow for a quick discharge of fluid stored therein), while piezoelectric valves corresponding to chambers of the pressure-mitigation device may be designed for high pressure and low flow. Moreover, some piezoelectric valves may support bidirectional fluid flow, while other piezoelectric valves may support unidirectional fluid flow. Generally, if the manifold includes unidirectional piezoelectric valves, each chamber in the pressure-mitigation device is associated with a pair of unidirectional piezoelectric valves to allow fluid flow in either direction. Here, for example, Chambers 1-3 are associated with a single bidirectional piezoelectric valve, Chamber 4 is associated with two bidirectional piezoelectric valves, and Chamber 5 is associated with two unidirectional piezoelectric valves.

The chambers of a pressure-mitigation device may be inflated/deflated for a predetermined duration of 15-180 seconds (e.g., 30 seconds, 60 seconds, 90 seconds, 120 seconds, 150 seconds, or any duration therebetween) in accordance with a predetermined pattern. Thus, the status of each chamber may be varied at least every 60 seconds, 90 seconds, 120 seconds, 240 seconds, etc. Generally, the predetermined pattern causes the chambers to be inflated/deflated in a non-identical manner. For example, if the pressure-mitigation device includes four chambers, the first and second chambers may be inflated for 30 seconds, the second and third chambers may be inflated for 45 seconds, the third and fourth chambers may be inflated for 30 seconds, and then the first and fourth chambers may be inflated for 45 seconds. These chambers may be inflated/deflated to a predetermined pressure level from 0-100 millimeters of mercury (mmHg) (e.g., 15 mmHg, 20 mmHg, 30 mmHg, 45 mmHg, 50 mmHg, or any pressure level therebetween). In some embodiments, the inflation pattern administered by the controller inflates/deflates two or more chambers at one time. In these embodiments, the chambers can be inflated/deflated to the same or different pressure levels, and the duration that the chambers are maintained at the pressure levels may be the same or different. For example, in the scenario above where the first and second chambers are inflated, the first chamber may be inflated to a pressure of 15 mm Hg while the second chamber may be inflated to a pressure of 30 mm Hg. In other embodiments, the controller can apply different inflation/deflation patterns to the individual chambers.

Methodologies for Relieving Pressure on a Human Body

FIG. 10 is a flow diagram of a process 1000 for varying the pressure in the chambers of a pressure-mitigation device that is positioned between a human body and a surface in accordance with embodiments of the present technology. By varying the pressure in the chambers, a controller can move the main point of pressure applied by the surface across the human body. For example, the main point of pressure applied by the support surface to the human body may be moved amongst multiple predetermined locations by sequentially varying the pressure in different predetermined subsets of chambers. Note that the human body could be in nearly any position, with minimal changes to the process 1000. Thus, the pressure-mitigation device may be arranged so that pressure is relieved an anatomical region located along the anterior or posterior side of the human body.

Initially, a controller can determine that a pressure-mitigation device has been connected to the controller (step 1001). The controller may detect which type of pressure-mitigation device has been connected by monitoring the connection between a fluid interface (e.g., the fluid interface 608 of FIG. 6B) and the pressure-mitigation device. Each type of pressure-mitigation device may include a different type of connector. For example, a pressure-mitigation device designed for deployment on elongated objects (e.g., pressure-mitigation apparatus 100 of FIGS. 1A-B) may include a first arrangement of magnets in its connector, and a pressure-mitigation apparatus designed for deployment on non-elongated objects (e.g., the pressure-mitigation apparatus of FIGS. 2A-B) may include a second arrangement of magnets in its connector. The controller may determine which type of pressure-mitigation apparatus has been connected based on which magnets have been detected within a specified proximity. As another example, the pressure-mitigation device designed for deployment on elongated objects may include a beacon capable of emitting a first electronic signature, while the pressure-mitigation device designed for deployment on non-elongated objects may include a beacon capable of emitting a second electronic signature. Examples of beacons include Bluetooth beacons, USB beacons, and infrared beacons. A beacon may be configured to communicate with the controller via a wired communication channel or a wireless communication channel.

The controller can then identify a pattern that is associated with the pressure-mitigation device (step 1002). For example, the controller may examine a library of patterns corresponding to different pressure-mitigation devices to identify the appropriate pattern. The library of patterns may be stored in a local memory (e.g., the memory 710 of FIG. 7) or a remote memory accessible to the controller across a network. The controller may modify an existing pattern based on the pressure-mitigation device, the user, the ailment affecting the user, etc. For example, the controller may alter an existing pattern responsive to determining that the pattern includes instructions for more chambers than the pressure-mitigation device includes. As another example, the controller may alter an existing pattern responsive to determining that the weight of the user exceeds a predetermined threshold.

In some embodiments, the pattern is associated with a characteristic of the user in addition to, or instead of, the pressure-mitigation device. For example, the controller may examine a library of patterns corresponding to different ailments or different anatomical regions to identify the appropriate pattern. Thus, the library may include patterns associated with anatomical regions along the anterior side of the human body, patterns associated with anatomical regions along the posterior side of the human body, or patterns associated with different ailments (e.g., ulcers, strokes, etc.).

The controller can then cause the chambers of the pressure-mitigation apparatus to be inflated in accordance with the pattern (step 1003). As discussed above, the controller can cause the pressure on one or more anatomical regions of the human body to be varied by controllably inflating one or more chambers, deflating one or more chambers, or any combination thereof.

Other steps may be performed in some embodiments. As an example, the controller may be configured to regulate inflation of the chambers based on a total duration of use of the pressure-mitigation device. For instance, the controller may increase or decrease the flow of air into the chambers (and thus the pressure of those chambers) in a continual, periodic, or ad hoc manner to account for extended applications of pressure on the human body. In some embodiments, the controller determines the total duration of use based on a clock signal generated by a clock module housed in the controller. In other embodiments, the controller determines the total duration of use based on signal(s) generated by some other computing device. For instance, the controller may be able to infer how long the pressure-mitigation device has been used based on the presence of a signal generated by a computing device associated with the patient, such as a mobile phone or wearable device. Said another way, the controller may infer the presence of the patient based on whether his/her computing device is located within a given proximity. For example, the controller may infer that the pressure-mitigation device has been is in use so long as the computing device is (1) presently detectable (e.g., via a point-to-point wireless channel, such as Bluetooth or Wi-Fi P2P) and (2) has been detectable for at least a certain amount of time (e.g., more than three minutes, five minutes, etc.).

Those skilled in the art will recognize that the approaches to mitigating the pressure described herein may be useful in various contexts. Several examples are provided below; however, these examples should not be construed as limiting in any sense. Instead, these examples are provided to illustrate the usefulness of mitigating pressure in a few different scenarios.

A. Mitigating Pressure on Patients Suffering from Respiratory Illnesses

FIG. 11 is a flow diagram of a process 1100 for improved treatment of a patient suffering from a respiratory illness. For the purpose of illustration, the processes below are described as being performed by a medical professional. However, those skilled in the art will recognize that some steps may be performed by the medical professional while other steps may be performed by the patient himself/herself. For example, the patient may be responsible for orienting himself/herself over a pressure-mitigation device able to mitigate pressure applied by the surface of an object such as a bed (e.g., an intensive care unit (ICU) bed). Similarly, those skilled in the art will recognize that a team of medical professionals could collectively perform these processes.

Initially, a medical professional can identify a patient who is a candidate for treatment of a respiratory illness (step 1101). The respiratory illness may be a chronic respiratory diseases (also referred to as a "chronic respiratory illness") such as chronic obstructive pulmonary disease (COPD), asthma, occupational lung disease, or pulmonary hypertension. Alternatively, the respiratory illness may be an acute respiratory disease (also referred to as an "acute respiratory infection") such as bronchitis, pneumonia, Severe Acute Respiratory Syndrome (SARS), Middle East Respiratory Syndrome (MERS), and coronavirus disease 2019 (COVID-19). The patient may be identified through conventional intake and diagnostic processes.

The medical professional can obtain a portable system that includes (i) a pressure-mitigation device that has a geometric arrangement of inflatable chambers and (ii) a controller configured to independently pressurize the inflatable chambers by regulating flow(s) of air (step 1102). As discussed above with respect to FIGS. 6A-C, the controller may include a handle for transportation of the portable system. Additionally or alternatively, the controller may be mountable on another structure, such as an IV pole or mobile workstation. Then, the medical professional can deploy the pressure-mitigation device on a surface on which the patient is to be immobilized (step 1103). Note that the term "immobilize," as used herein, may be used to refer to patients who are partially or completely immobilized. A patient could be completely immobilized due to, for example, anesthesia or physical restraints, while a patient could be partially immobilized due to the presence of pillows, rails (e.g., along the side of a bed), armrests (e.g., along the side of a chair), and the like.

Thereafter, the medical professional can orient the patient in a prone position such that an anterior anatomical region is located adjacent the pressure-mitigation device (step 1104). For example, the medical professional may orient the patient such that the thorax is located adjacent a target region of the geometric arrangement.

Orienting the patient in the appropriate position may involve constraining the patient with a structural feature that is located near (e.g., adjacent to) the surface. In some embodiments, the structural feature is part of the object of which the surface is a part. For example, the structural feature may be a rail that extends longitudinally along a bed in which the patient is positioned, or the structural feature may be an armrest of a chain is which the patient is positioned. In other embodiments, the structural feature is separate from the underlying object. For example, a patient may be constrained within a bed by placing pillows along each side of the body that inhibit horizontal movement toward either side of the bed.

Then, the medical professional can cause the portable system to shift a point of pressure applied by the surface to the anterior anatomical region by pressurizing the inflatable chambers to varying degrees in accordance with a programmed pattern (step 1105). For example, the medical professional may indicate (e.g., via an interface or input component) that the patient is properly oriented, and thus pressurization of the inflatable chambers should commence. In some embodiments, the controller is configured to regulate the flow(s) of air into the inflatable chambers based on a characteristic of the patient or the underlying object. For example, the controller may regulate the flow(s) of air based on the weight of the patient. Accordingly, in such embodiments, the medical professional may be prompted to input the weight of the patient via an interface generated by the controller.

Historically, some patients suffering from respiratory illnesses—especially those who are immobilized—have been periodically turned by medical professionals to improve health outcomes (e.g., by lessening the likelihood of developing ulcers). This procedure is tedious, and it can be difficult to execute consistently and properly (e.g., due to the weight of the patient). Some embodiments of the portable system described herein are designed to facilitate this procedure. For example, the portable system may be configured to periodically generate notifications that indicate when a treatment regimen requires the patient be turned. These notifications may be visual notifications or audible notifications. Accordingly, upon discovering a notification has been generated, the medical professional may orient the patient in a supine position such that a posterior anatomical region is located adjacent the pressure-mitigation device. If the patient is initially oriented in a prone position, as described with reference to FIG. 12, then the notification may be representative of an instruction to orient the patient in the supine position. Note that notifications may be generated periodically (e.g., every one, two, or four hours) so that the patient is periodically turned from the prone position to the supine position, or vice versa. Consistent mitigation of pressure by the pressure-mitigate device may allow the patient to be turned less frequently than would conventionally be recommended.

FIG. 12 is a flow diagram of another process 1200 for improved treatment of a patient suffering from a respiratory illness. Steps 1201-1203 of FIG. 12 may be substantially similar to steps 1101-1103 of FIG. 11. Here, however, the medical professional orients the patient in a supine position such that a posterior anatomical region is located adjacent the pressure-mitigation device (step 1204). For example, the medical professional may orient the patient such that the sacral region is located adjacent a target region of the geometric arrangement of inflatable chambers.

Then, the medical professional can cause the portable system to shift a point of pressure applied by the surface to the posterior anatomical region by pressuring the inflatable chambers to varying degrees in accordance with a programmed pattern (step 1205). The programmed pattern may cause be designed such that voids are created beneath known anatomical structures within, or proximate to, the posterior anatomical region in a predetermined (e.g., repetitive or non-repetitive) manner. In some embodiments, programmed pattern is representative of a non-repeating algorithm that considers data indicative of pressure of each inflatable chamber of the pressure-mitigation device. Thus, the controller may determine how to inflate the chambers based on the pressure of those chambers to account for movement of the patient in real time. As discussed above, the programmed pattern may be associated with the posterior anatomical region on which pressure is to be relieved. Accordingly, if the patient is reoriented (e.g., into the prone position), then the controller may pressurize the inflatable chambers in accordance with a different programmed pattern.

Sometime thereafter, the medical professional may receive an indication that a treatment regimen has been completed (step 1206). For example, the indication may be representative of an electronic notification (also referred to as a "digital notification") generated by a network-accessible server system that is communicatively connected to the portable system. The digital notification could be received on, for example, a computing device associated with the medical professional. As another example, the indication may be representative of an audible notification or a visual notification that is generated by the portable system. Upon receiving the indication, the medical professional may remove the pressure-mitigation device from the surface responsive to determining that the patient is no longer positioned on the underlying object (step 1207). Note that the patient may need to be moved from the surface before this occurs in some instances (e.g., where the patient is unconscious, under anesthesia, etc.).

B. Mitigating Pressure on Immobilized Patients

FIG. 13 is a flow diagram of a process 1300 for improved treatment of a patient undergoing extracorporeal membrane oxygenation (ECMO) treatment. As part of treatment, an ECMO machine that replaces the function of the heart and lungs can be used. Patients who require ECMO treatment normally have severe, life-threatening illnesses that prevent the heart and lungs from working properly. For example, ECMO treatment may be used upon discovering severe lung damage from infection or shock following a massive heart attack. Patients are typically supported by ECMO machines for several hours to several days, and thus are good candidates for treatment with the systems described herein.

Initially, a medical professional can identify a patient who is a candidate for ECMO treatment (step 1301). The patient may be identified through conventional intake and diagnostic processes. Thus, the patient may be identified for a candidate for ECMO treatment, and then the medical professional may separately determine that treatment with a portable system is appropriate based on, for example, a characteristic of the ECMO treatment (e.g., duration) or a characteristic of the patient (e.g., weight, comorbidities). Steps 1302-1303 of FIG. 13 may be substantially similar to steps 1102-1103 of FIG. 11.

Then, the medical professional may orient the patient such that an anatomical region of the patient is located adjacent the pressure-mitigation device (step 1304) and then determine that a cannulation operation in which at least two tubes are inserted into the patient has been completed (step 1305). Generally, the location of the anatomical region (i.e., whether the anatomical region is located along the anterior or posterior side of the patient) depends on the location of these tubes. Thus, the pressure-mitigation device may alleviate pressure along the anterior side of the patient while in the prone position, or the pressure-mitigation device may alleviate pressure along the posterior side of the patient while in the supine position. In some embodiments, the medical professional (or some other medical professional) may be responsible for performing the cannulation operation. Thus, the medical professional may insert the tubes into the neck, chest, or legs of the patient (step 1306) and then connect the tubes to an ECMO machine configured to oxygenate blood that is obtained from, and then returned to, the patient (step 1307).

After completing the cannulation operation, the medical professional can cause the portable system to shift a point of pressure applied by the surface to the anatomical region by pressurizing the inflatable chambers to varying degrees in accordance with a programmed pattern (step 1308). The programmed pattern may vary based on where the tubes (e.g., the ingress and egress tubes) were inserted into the patient. Thus, the medical professional may be prompted (e.g., by an interface of the controller) to input locations where the tubes were inserted into the patient. Generally, if the tubes are inserted along the anterior side of the patient, then the patient will be oriented in the supine position along the surface. Conversely, if the tubes are inserted along the posterior side of the patient, then the patient will normally be oriented in the prone position. The chambers of the pressure-mitigation device may be inflated and/or deflated in different orders or to different pressures depending on whether the patient is in the supine or prone position.

FIG. 14 is a flow diagram of a process 1400 for improved treatment of a patient presently being treated with a mechanical ventilator. Ventilators (also referred to as "breathing machines" or "respirators") help get oxygen into the lungs and remove carbon dioxide from the body. Like ECMO machines, ventilators are normally used for several hours to several days, and thus may be used in conjunction with the systems described herein to significant effect.

Initially, a medical professional can identify a patient who is a candidate for treatment with a mechanical ventilator (step 1401). The patient may be identified through conventional intake and diagnostic processes. Thus, the patient may be identified for a candidate for treatment with a mechanical ventilator, or the patient may already be undergoing treatment with a mechanical ventilator. In either case, the medical professional may determine that treatment with a portable system is appropriate based on, for example, a characteristic of the ventilator treatment (e.g., duration) or a characteristic of the patient (e.g., weight, comorbidities). Steps 1402-1403 of FIG. 14 may be substantially similar to steps 1102-1103 of FIG. 11.

Then, the medical professional may orient the patient such that an anatomical region of the patient is located adjacent the pressure-mitigation device (step 1404) and then determine that the patient has been connected to a mechanical ventilator (step 1405). In some embodiments, the medical professional (or some other medical professional) may be responsible for deploying the mechanical ventilator. Thus, the medical professional may anesthetize the patient so as to induce a loss of consciousness (step 1406) and then intubate the patient by inserting a tube that is connected to the mechanical ventilator into the trachea (step 1407). Generally, the patient is anesthetized after being oriented on the pressure-mitigation device, and then intubated after being anesthetized.

The location of the anatomical region (i.e., whether the anatomical region is located along the anterior or posterior side of the patient) may depend on the location of the tube extending from the trachea to the mechanical ventilator. For example, the pressure-mitigation device may alleviate pressure along the anterior side if the patient is in the prone position, or the pressure-mitigation device may alleviate pressure along the posterior side if the patient is in the supine position.

After the patient has been connected to the mechanical ventilator, the medical professional can cause the portable system to shift a point of pressure applied by the surface to the anatomical region by pressurizing the inflatable chambers to varying degrees in accordance with a programmed pattern (step 1408). Such an approach to relieving pressure may lessen or obviate the need to periodically turn the patient (e.g., from the prone to supine position, or vice versa). This not only saves significant amounts of time and resources, but also lessens the likelihood of complications due to turning such as dislodged tracheal tubes.

The programmed pattern may vary based on where the tubes (e.g., the ingress and egress tubes) were inserted into the patient. Thus, the medical professional may be prompted (e.g., by an interface of the controller) to input locations where the tubes were inserted into the patient. Generally, if the tubes are inserted along the anterior side of the patient, then the patient will be oriented in the supine position along the surface. Conversely, if the tubes are inserted along the posterior side of the patient, then the patient will normally be oriented in the prone position. The chambers of the pressure-mitigation device may be inflated and/or deflated in different orders or to different pressures depending on whether the patient is in the supine or prone position.

As further discussed below, the portable system (and, more specifically, the controller) may be communicatively connected to the mechanical ventilator in some embodiments. In such embodiments, the controller may regulate pressure of the inflatable chambers based on a frequency at which the mechanical ventilator pushes air into the lungs of the patient. Thus, the inflatable chambers may be pressurized such that the patient is moved only while air is being pushed into the lungs, only while carbon dioxide is being removed from the lungs, in between these actions, or any combination thereof.

Overview of Pressure-Mitigation Systems

Figure 15:
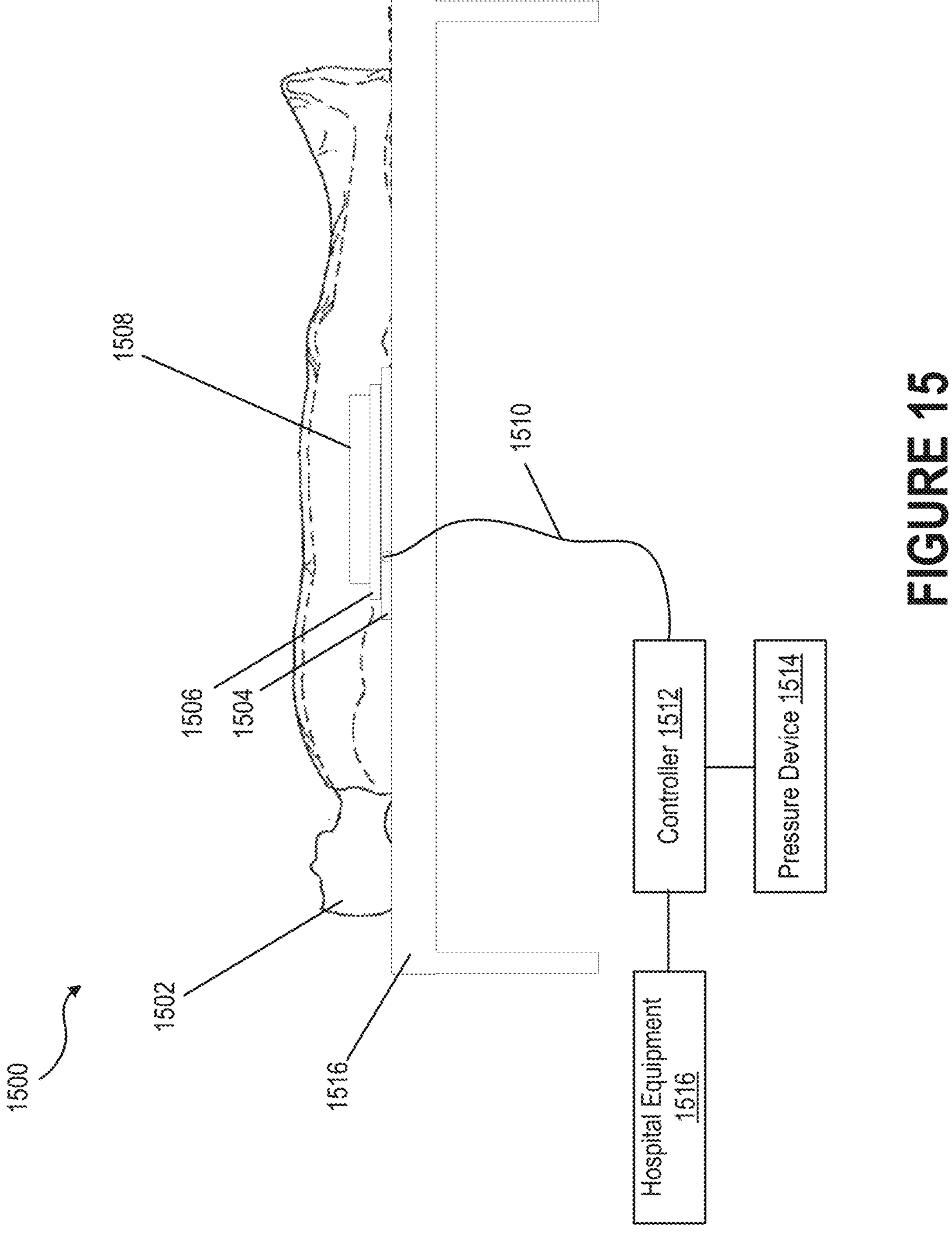
FIG. 15 is a partially schematic side view of a pressure-mitigation system for orienting a patient over a pressure-mitigation device in accordance with embodiments of the present technology.

FIG. 15 is a partially schematic side view of a pressure-mitigation system 1500 (or simply "system") for orienting a patient 1502 (also referred to as a "user") over a pressure-mitigation device 1506 in accordance with embodiments of the present technology. Here, the system 1500 includes a pressure-mitigation device 1506 that include side supports 1508, an attachment device 1504, a pressure device 1514, and a controller 1512. Other embodiments of the system 1500 may include a subset of these components. For example, the system 1500 may include a pressure-mitigation device 1506, a pressure device 1514, and a controller 1512. The pressure-mitigation device 1506 is discussed in further detail with respect to FIGS. 1A-3, and the controller 1512 is discussed in further detail with respect to FIGS. 6A-9.

Figure 16A:
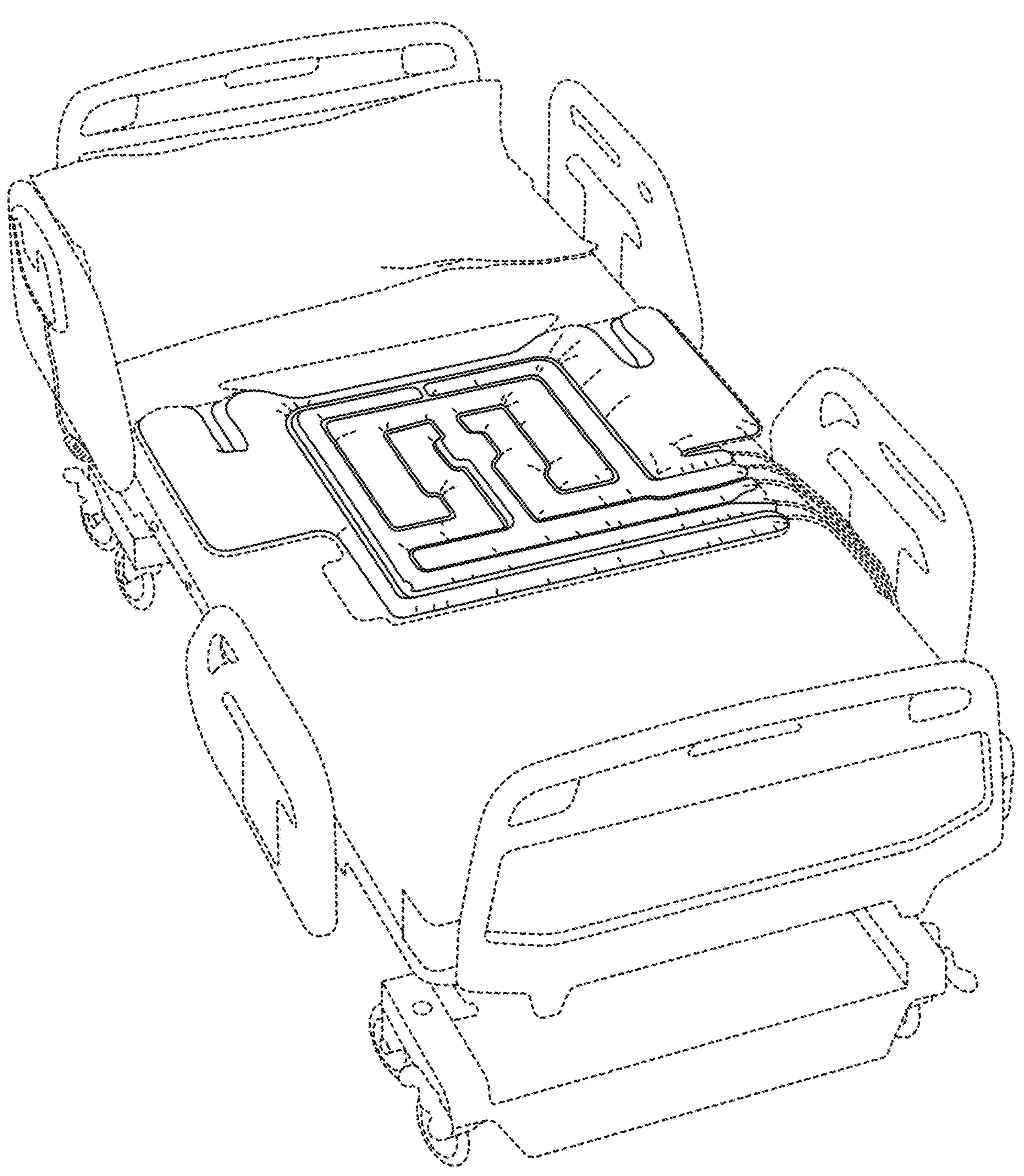
FIG. 16A illustrates an example of a pressure-mitigation device that includes a pair of elevated side supports that has been deployed on the surface of an object (here, a hospital bed).
Figure 16B:
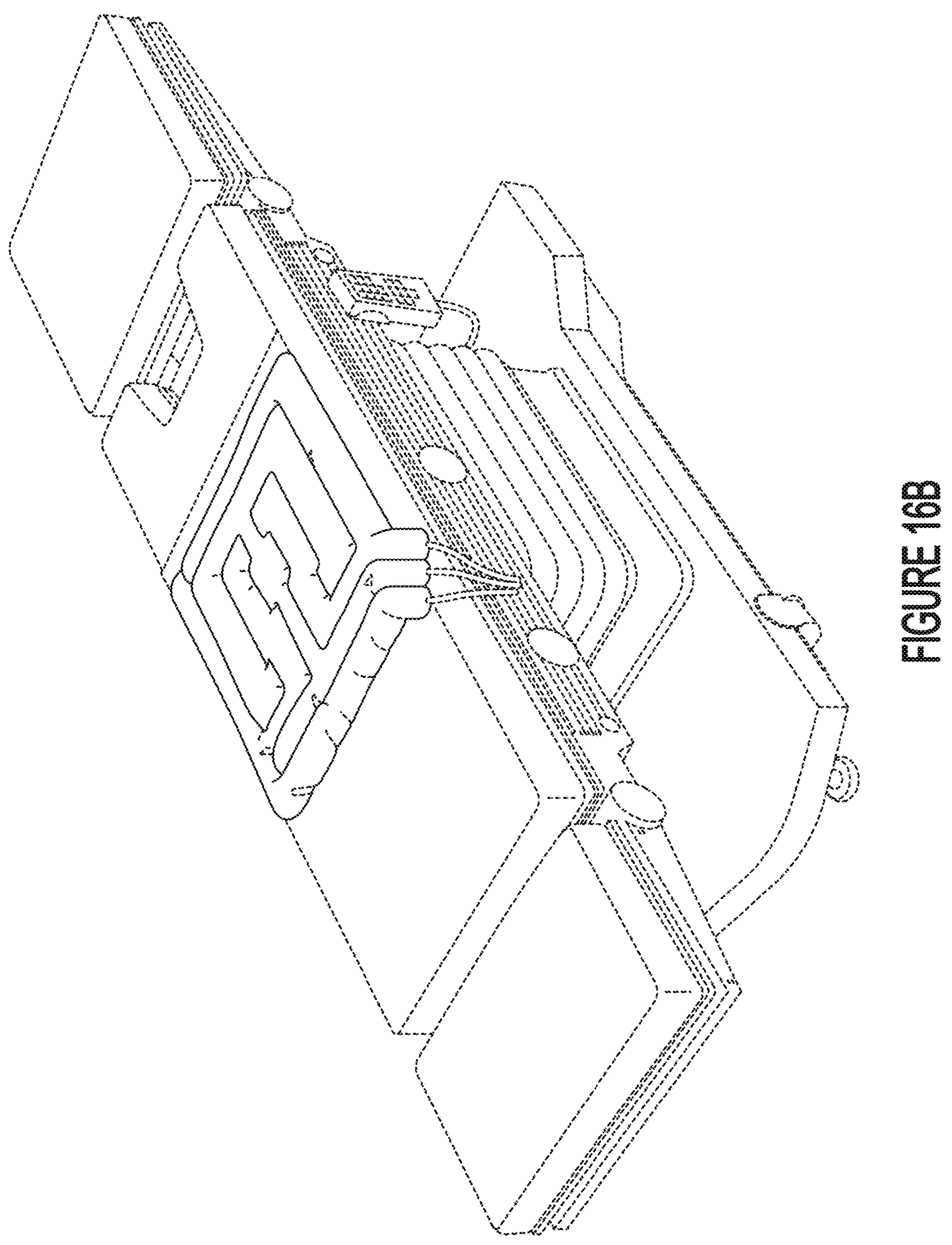
FIG. 16B illustrates an example of a pressure-mitigation device with no elevated side supports that has deployed on the surface of an object (here, an operating table).

In this embodiment, the pressure-mitigation device 1506 includes a pair of elevated side supports 1508 that extend longitudinally along opposing sides of the pressure-mitigation device 1506. FIG. 16A illustrates an example of a pressure-mitigation device that includes a pair of elevated side supports that has been deployed on the surface of an object (here, a hospital bed). However, some embodiments of the pressure-mitigation device 1506 do not include any elevated side supports. For example, side supports may not be necessary if the object on which the user 1502 is positioned includes lateral structures that prevent or inhibit horizontal movement, or if the user 1502 will be completely immobilized (e.g., using anesthesia). FIG. 16B illustrates an example of a pressure-mitigation device with no elevated side supports that has deployed on the surface of an object (here, an operating table). The pressure-mitigation device 1506 includes a series of chambers interconnected on a base material that may be arranged in a geometric pattern designed to mitigate the pressure applied to an anatomical region by the surface of the object 1516.

The elevated side supports 1508 can be configured to actively orient the anatomical region of the user 1502 over the series of chambers. For example, the elevated side supports 1508 may be responsible for actively orienting the anatomical region widthwise over the epicenter of the geometric pattern. As shown in FIG. 15, the anatomical region may be the sacral region. However, the anatomical region could be any region of the human body that is susceptible to pressure. The elevated side supports 1508 may be configured to be ergonomically comfortable. For example, the elevated side supports 1508 may include a recess designed to accommodate the forearm that permits pressure to be offloaded from the elbow. The elevated side supports 1508 may be significantly larger in size than the chambers of the pressure-mitigation device 1506. Accordingly, the elevated side supports 1508 may create a barrier that restricts lateral movement of the user 1502. In some embodiments, the elevated side supports are approximately 2-3 inches taller in height as compared to the average height of an inflated chamber. Because the elevated side supports 1506 straddle the user 1502, the elevated side supports 1508 can act as barriers for maintaining the position of the user 1502 on top of the pressure-mitigation device 1506. As discussed above, the elevated side supports 1508 may be omitted in some embodiments. For example, the elevated side supports 1508 may be omitted if the user 1502 suffers from impaired mobility due to physical injury, structural components that limit movement, anesthesia, or some other condition that limits natural movement.

In some embodiments, the inner side walls of the elevated side supports 1508 form, following inflation, a firm surface at a steep angle of orientation with respect to the pressure-mitigation device 1506. For example, the inner side walls may be on a plane of approximately 115 degrees, plus or minus 24 degrees, from the plane of the pressure-mitigation device 1506. These steep inner side walls can form a channel that naturally positions the user 1502 over the chambers of the pressure-mitigation device 1506. Thus, inflation of the elevated side supports 1508 may actively force the user 1502 into the appropriate position for mitigating pressure by orienting the body in the correct location with respect to the chambers of the pressure-mitigation device 1506.

After the initial inflation cycle has been completed, the pressure of each elevated side support 1508 may be lessened to increase comfort and prevent excessive force against the lateral sides of the user 1502. Oftentimes, a medical professional will be present during the initial inflation cycle to ensure that the elevated side supports 1508 properly position the user 1502 over the pressure-mitigation device 1506.

The controller 1512 can be configured to regulate the pressure of each chamber in the pressure-mitigation device 1506 (and the elevated side supports 1508, if included) via one or more flows of air generated by a pressure device 1514. One example of a pressure device is an air pump. These flow(s) of air can be guided from the controller 1512 to the pressure-mitigation device 1506 via multi-channel tubing 1510. For example, the chambers may be controlled in a specific pattern to preserve blood flow and reduce pressure applied to the user 1502 when inflated (i.e., pressurized) and deflated (i.e., depressurized) in a coordinated fashion by the controller 1512. As shown in FIG. 15, the multi-channel tubing 1510 may be connected between the pressure-mitigation device 1506 and the controller 1512. Accordingly, the pressure-mitigation device 1506 may be fluidically coupled to a first end of tubing (e.g., single-channel tubing or multi-channel tubing) while the controller 1512 may be fluidically coupled to a second end of the tubing. While the pressure device 1512 is normally housed within the controller 1512, these components are also connected via multi-channel tubing in some embodiments. Thus, the pressure device 1514 may be fluidically coupled to a first end of multi-channel tubing while the controller 1506 may be fluidically coupled to a second end of multi-channel tubing.

As discussed above, some embodiments of the system 1500 include a communication module configured to facilitate wireless communication with nearby computing devices. For example, the controller 1512 may include a communication module able to wirelessly communicate with hospital equipment 1516 involved in treatment of the user 1502. Examples of hospital equipment include ECMO machines, mechanical ventilators, mobile workstations, monitors, and the like. The controller 1512 may be able to pressurize the inflatable chambers of the pressure-mitigation device 1506 based on information obtained from the hospital equipment. For instance, the controller 1512 may alter a programmed pattern for pressurizing the inflatable chambers based on the current status of the hospital equipment 1506, whether the hospital equipment 1506 indicates that there is a problem, etc. As an example, the controller 1512 may receive, via the communication module, input from an ECMO machine indicating that treatment has been halted. Upon receiving the input, the controller 1512 may cause all inflatable chambers of the pressure-mitigation device 1506 to be pressurized (i.e., inflated) or depressurized (i.e., deflated) for easier management of the user 1502. As another example, the controller 1512 may receive, via the communication module, input from a mechanical ventilator that a procedure (e.g., suctioning, spraying of medication, bronchoscopy) will be performed. In such a scenario, the controller 1512 may cause all inflatable chambers of the pressure-mitigation device 1506 to be pressurized (i.e., inflated) or depressurized (i.e., deflated) so that the procedure is easier to perform. Thus, the controller 1512 may discontinue treatment in accordance with the programmed pattern responsive to determining that it is not safe, appropriate, or desirable to continue treatment.

Processing System

Figure 17:
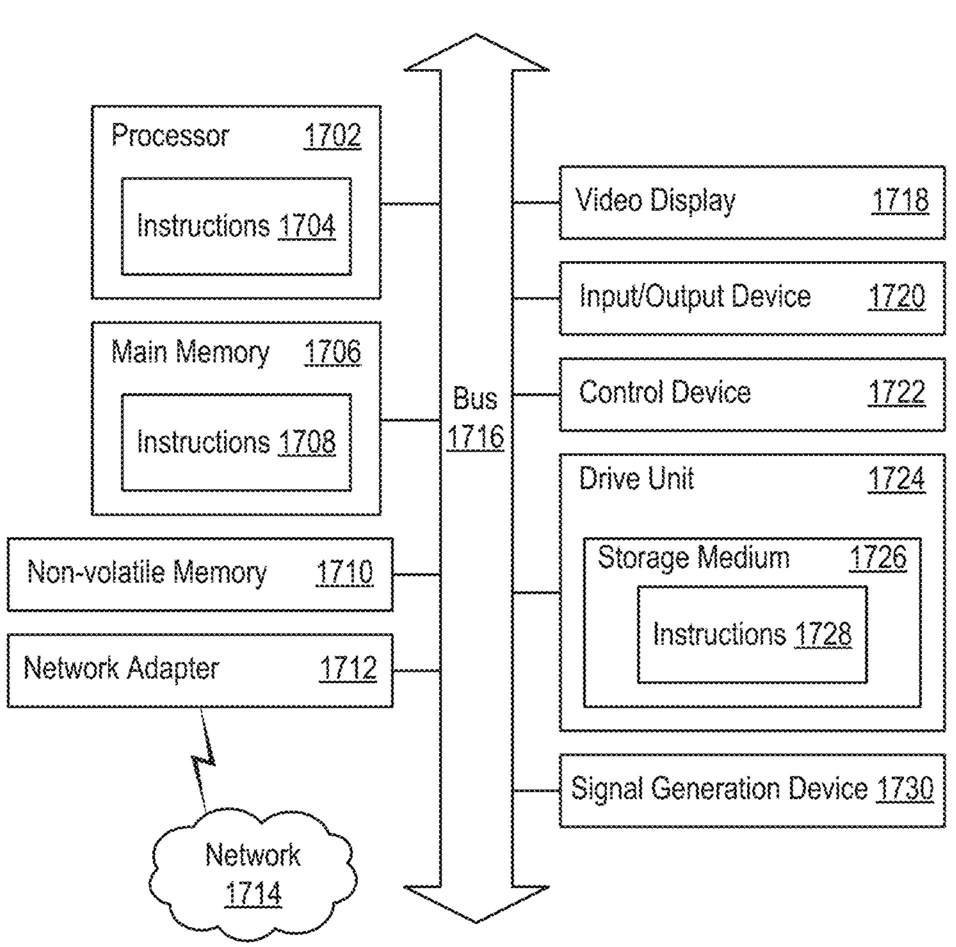
FIG. 17 is a block diagram illustrating an example of a processing system in which at least some operations described herein can be implemented.

FIG. 17 is a block diagram illustrating an example of a processing system 1700 in which at least some operations described herein can be implemented. For example, components of the processing system 1700 may be hosted on a controller (e.g., controller 1512 of FIG. 15) responsible for controlling the flow of fluid to a pressure-mitigation device (e.g., pressure-mitigation apparatus 1506 of FIG. 15). As another example, components of the processing system 1700 may be hosted on a computing device that is communicatively coupled to the controller.

The processing system 1700 may include a processor 1702, main memory 1706, non-volatile memory 1710, network adapter 1712 (e.g., a network interface), video display 1718, input/output device 1720, control device 1722 (e.g., a keyboard, pointing device, or mechanical input such as a button), drive unit 1724 that includes a storage medium 1726, or signal generation device 1730 that are communicatively connected to a bus 1716. The bus 1716 is illustrated as an abstraction that represents one or more physical buses and/or point-to-point connections that are connected by appropriate bridges, adapters, or controllers. The bus 1716, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit ($I^2C$) bus, or bus compliant with Institute of Electrical and Electronics Engineers (IEEE) Standard 1394.

The processing system 1700 may share a similar computer processor architecture as that of a computer server, router, desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify action(s) to be taken by the processing system 1700.

While the main memory 1706, non-volatile memory 1710, and storage medium 1724 are shown to be a single medium, the terms "storage medium" and "machine-readable medium" should be taken to include a single medium or multiple media that stores one or more sets of instructions 1726. The terms "storage medium" and "machine-readable medium" should also be taken to include any medium that is capable of storing, encoding, or carrying a set of instructions for execution by the processing system 1700.

In general, the routines executed to implement the embodiments of the present disclosure may be implemented as part of an operating system or a specific application, component, program, object, module, or sequence of instructions (collectively referred to as "computer programs"). The computer programs typically comprise one or more instructions (e.g., instructions 1704, 1708, 1728) set at various times in various memories and storage devices in a computing device. When read and executed by the processor 1702, the instructions cause the processing system 1700 to perform operations to execute various aspects of the present disclosure.

While embodiments have been described in the context of fully functioning computing devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile and non-volatile memory devices 1710, removable disks, hard disk drives, optical disks (e.g., Compact Disk Read-Only Memory (CD-ROMS) and Digital Versatile Disks (DVDs)), cloud-based storage, and transmission-type media such as digital and analog communication links.

The network adapter 1712 enables the processing system 1700 to mediate data in a network 1714 with an entity that is external to the processing system 1700 through any communication protocol supported by the processing system 1700 and the external entity. The network adapter 1712 can include a network adaptor card, a wireless network interface card, a switch, a protocol converter, a gateway, a bridge, a hub, a receiver, a repeater, or a transceiver that includes an integrated circuit (e.g., enabling communication over Bluetooth or Wi-Fi).

The techniques introduced here can be implemented using software, firmware, hardware, or a combination of such forms. For example, aspects of the present disclosure may be implemented using special-purpose hardwired (i.e., non-programmable) circuitry in the form of application-specific integrated circuits (ASICs), programmable logic devices (PLDs), field-programmable gate arrays (FPGAs), and the like.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:

identifying a patient who is a candidate for extracorporeal membrane oxygenation (ECMO) treatment;

obtaining a portable system that includes— a pressure-mitigation device that includes chambers that are independently inflatable, and a controller that is configured to controllably inflate each of the chambers by regulating one or more flows of air;

deploying the pressure-mitigation device on a surface on which the patient is to be immobilized;

orienting the patient such that an anatomical region is located adjacent the pressure-mitigation device;

performing a cannulation operation by inserting at least two tubes into the neck, chest, or legs of the patient;

connecting the at least two tubes to an ECMO machine that is configured to oxygenate blood that is obtained from, and then returned to, the patient;

inputting locations where the at least two tubes were inserted into the patient via an interface that is generated by the controller; and in response to a determination that the cannulation operation has been completed, causing the portable system to shift pressure that is applied by the surface to the anatomical region by inflating the chambers to varying degrees over time in accordance with a programmed pattern that is based on the locations.

2. The method of claim 1, wherein the pressure-mitigation device is designed to alleviate pressure along an anterior side of the patient while in a prone position.

3. The method of claim 1, wherein the pressure-mitigation device is designed to alleviate pressure along a posterior side of the patient while in a supine position.

4. The method of claim 1, wherein said orienting involves constraining the patient with a structural feature that is located adjacent the surface.

5. The method of claim 1, wherein the pressure-mitigation device includes a pair of side supports that are configured to orient the patient over the chambers, and wherein said orienting involves the controller inflating at least one of the pair of side supports.

6. A method for treating a patient who is a candidate for extracorporeal membrane oxygenation (ECMO) treatment, the method comprising:

deploying a pressure-mitigation device that includes multiple chambers that are independently inflatable on a surface on which the patient is to be immobilized during the ECMO treatment;

connecting the pressure-mitigation device to a controller that is configured to controllably inflate the multiple chambers over time by regulating one or more flows of air;

orienting the patient such that a given anatomical region is located above the pressure-mitigation device;

inputting, via an interface that is presented by the controller, locations where at least two tubes are inserted into the patient as part of a cannulation operation; and in response to a determination that the cannulation operation has been completed, causing the controller to shift a pressure that is applied by the surface to the given anatomical region through varied inflation of the multiple chambers over time, wherein the controller inflates the multiple chambers in accordance with a programmed pattern that is associated with the locations.

7. The method of claim 6, wherein said connecting comprises attaching tubing between one or more fluid egress interfaces of the controller and one or more fluid ingress interfaces of the pressure-mitigation device.

8. The method of claim 6, wherein the controller inflates the multiple chambers in accordance with a programmed pattern that is associated with the given anatomical region.

9. The method of claim 6, wherein the controller inflates the multiple chambers in accordance with a programmed pattern that is associated with a characteristic of the patient.

10. The method of claim 6, wherein the pressure-mitigation device further includes a pair of chambers that extend longitudinally along opposing sides of the multiple chambers, and wherein the method further comprises:

in response to a determination that the patient is situated on the pressure-mitigation device, causing the pair of chambers to be inflated to facilitate orienting the given anatomical region over a central portion of the pressure-mitigation device.

11. The method of claim 6, wherein said orienting comprises constraining the patient with a structural feature that is located adjacent the surface.

12. The method of claim 11, wherein the structural feature is part of a same structure as the surface.

13. A non-transitory medium with instructions stored thereon that, when executed by a processor housed in a controller, cause the controller to perform operations comprising:

receiving first input that indicates a pressure-mitigation device with multiple chambers has been fluidly coupled to the controller;

receiving second input that indicates a patient has been situated on the pressure-mitigation device such that a given anatomical region is located above the pressure-mitigation device;

receiving third input that indicates the patient has begun receiving extracorporeal membrane oxygenation (ECMO) treatment from an ECMO machine;

receiving fourth input that specifies locations where at least two tubes were inserted into the neck, chest, or legs of the patient as part of a cannulation operation;

identifying a programmed pattern for inflating the multiple chambers by either:

selecting the programmed pattern from among multiple programmed patterns based on the locations, or adjusting a default programmed pattern to account for the locations; and regulating multiple flows of air, each of which is destined for a corresponding one of the multiple chambers, in accordance with the programmed pattern.

14. The non-transitory medium of claim 13, wherein a first one of the multiple programmed patterns is associated with the patient being in a supine position, and wherein a second one of the multiple programmed patterns is associated with the patient being in a prone position.

15. A non-transitory medium with instructions stored thereon that, when executed by a processor housed in a controller, cause the controller to perform operations comprising:

receiving first input that indicates a pressure-mitigation device with multiple chambers has been fluidly coupled to the controller, wherein the first input is representative of a signal that is generated by a sensor located proximate an egress interface through which air leaves the controller and that indicates a number or an arrangement of magnets in a tube that is connectable to the egress interface and through which the air is guided to the pressure-mitigation device;

receiving second input that indicates a patient has been situated on the pressure-mitigation device such that a given anatomical region is located above the pressure-mitigation device;

receiving third input that indicates the patient has begun receiving extracorporeal membrane oxygenation (ECMO) treatment from an ECMO machine;

receiving fourth input that specifies locations where at least two tubes were inserted into the neck, chest, or legs of the patient as part of a cannulation operation; identifying a programmed pattern for inflating the multiple chambers by either: selecting the programmed pattern from among multiple programmed patterns based on the locations, or adjusting a default programmed pattern to account for the locations;

and regulating multiple flows of air, each of which is destined for a corresponding one of the multiple chambers, in accordance with a programmed pattern that is selected or altered to account for the patient receiving the ECMO treatment.

16. The non-transitory medium of claim 15, wherein a first one of the multiple programmed patterns is associated with the patient being in a supine position, and wherein a second one of the multiple programmed patterns is associated with the patient being in a prone position.

* * * * *